(12) United States Patent
Yamamoto et al.

(10) Patent No.: US 10,357,160 B2
(45) Date of Patent: Jul. 23, 2019

(54) IMAGE ACQUIRING APPARATUS, SYSTEMS, AND METHODS

(71) Applicant: Canon U.S.A., Inc., Melville, NY (US)

(72) Inventors: Akira Yamamoto, Ageo (JP); Mitsuhiro Ikuta, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 15/725,779

(22) Filed: Oct. 5, 2017

(65) Prior Publication Data

US 2019/0104941 A1 Apr. 11, 2019

(51) Int. Cl.
*G01N 21/53* (2006.01)
*A61B 5/00* (2006.01)
(Continued)

(52) U.S. Cl.
CPC ........ *A61B 5/0075* (2013.01); *A61B 1/00009* (2013.01); *A61B 1/00096* (2013.01);
(Continued)

(58) Field of Classification Search
CPC ................ G02B 23/2469; G02B 23/26; G02B 23/2423; G02B 27/48; G02B 23/2453;
(Continued)

(56) References Cited

U.S. PATENT DOCUMENTS 4,965,441 A 10/1990 Picard
6,341,036 B1 1/2002 Tearney et al.
(Continued)

FOREIGN PATENT DOCUMENTS

JP 05-157628 A 6/1993
JP 1993157628 A 6/1993
(Continued)

OTHER PUBLICATIONS

Kang, D., et al., "Spectrally-encoded color imaging", Optics Express, Aug. 17, 2009, pp. 15239-15247, vol. 17, No. 17.
(Continued)

*Primary Examiner* — Michael P Stafira
(74) *Attorney, Agent, or Firm* — Canon U.S.A., Inc. I.P. Division

(57) ABSTRACT

Two-dimensional image acquiring apparatuses, systems, methods and storage mediums are provided herein. An apparatus includes a Spectrally Encoded Endoscopy ("SEE") probe including a diffractive element, the diffractive element operating to separate and diffract a transmitted light into separated light beams such that the diffracted light beams are superposed or substantially superposed on a target region; an image sensor that operates to acquire one or more intensities from a detected light; and an imaging optical system that operates to image light beams separated from the detected light, wherein the diffractive element, the imaging optical system, and the sensor are disposed for each of the light beams separated from the detected light to acquire spectral data of each of the light beams separated from the detected light. The diffractive element operates to rotate such that an image of the image sensor is changed, and a two-dimensional image is acquired.

20 Claims, 12 Drawing Sheets

(51) Int. Cl.
*A61B 1/00* (2006.01)
*H04N 5/225* (2006.01)
*A61B 1/05* (2006.01)
*G01N 21/552* (2014.01)

(52) U.S. Cl.
CPC .............. *A61B 1/05* (2013.01); *A61B 5/0062* (2013.01); *A61B 5/0084* (2013.01); *H04N 5/2256* (2013.01); *G01N 21/553* (2013.01); *H04N 2005/2255* (2013.01)

(58) Field of Classification Search
CPC ...... G02B 26/10; G02B 6/02; G02B 6/02042; G02B 6/036; G02B 6/03605; G02B 6/03622; G02B 6/03638; G02B 6/4298; G02B 5/18; G02B 23/2461; G02B 6/32; G02B 21/0028; G02B 21/0064; G02B 23/243; G02B 26/12; G02B 3/0087; G02B 6/34; G02B 23/24; G02B 23/2476; G02B 27/4227; G02B 27/425; G02B 5/1852; G02B 5/1857; G02B 6/02076; G02B 6/02085; G02B 6/138; G02B 6/241; G02B 6/29311; G02B 6/29341; G02B 6/3604; G02B 21/0008; G02B 21/0036; G02B 21/0048; G02B 21/0052; G02B 21/0076; G02B 21/361; G02B 2207/117; G02B 23/02; G02B 23/2407; G02B 26/002; G02B 26/103; G02B 26/105; G02B 26/106; G02B 27/1086; G02B 27/4244; G02B 27/4294; G02B 5/1814; G02B 5/1847; G02B 5/1866; G02B 6/03633; G02B 6/2746; G02B 6/2821; G02B 6/2835; G02B 6/2861; G02B 6/29313; G02B 6/2934; G01J 3/0218; G01J 3/0208; G01J 3/02; G01J 3/18; G01J 3/0256; G01J 3/2823; G01J 3/0205; G01J 3/10; G01J 3/021; G01J 3/453; G01J 9/0215; G01J 3/024; G01J 3/0264; G01J 3/1804; G01J 3/1895; G01J 3/44; G01J 3/443; G01J 3/45; G01J 2003/1286; G01J 2009/0265; G01J 3/0262; G01J 3/06; G01J 3/2803; G01J 3/36; G01J 3/433; G01J 3/4338; G01J 3/4406; G01J 3/4412; G01J 3/4532; G01J 3/4537; G01B 9/02091; G01B 9/02044; G01B 9/02004; G01B 2290/45; G01B 2290/70; G01B 9/02002; G01B 9/02083; G01B 9/02014; G01B 9/02027; G01B 9/02028; G01B 9/02081; G01B 9/02087; G01B 9/0209; G01B 2290/20; G01B 9/02; G01B 9/02005; G01B 9/02007; G01B 9/02008; G01B 9/02043; G01B 9/02049; G01B 9/0205; G01B 9/02064; G01B 9/02068; G01B 9/02072; G01B 9/02075; G01B 9/02084; G01B 9/04; G01B 11/2441; G01B 2290/35; G01B 2290/65; G01B 9/0201; G01B 9/02011; G01B 9/02029; G01B 9/02036; G01B 9/02037; G01B 9/02058; G01B 9/02063; G01B 9/02067; G01B 9/02069; G01B 9/02082; G01B 9/02085; G01N 21/4795; G01N 21/474; G01N 21/47; G01N 2021/6484; G01N 21/645; G01N 21/6456; G01N 21/6458; G01N 21/27; G01N 21/55; G01N 21/64; G01N 21/6486; G01N 21/65; G01N 2021/1765; G01N 2021/1787; G01N 2021/6417; G01N 2021/6421; G01N 2021/653; G01N 21/25; G01N 21/7746; G01N 2201/084; G01N 2201/0866; G01N 2223/419; G01N 33/4833; G01N 11/00; G01N 2011/006; G01N 2021/1725; G01N 2021/1782; G01N 2021/3595; G01N 2021/4742; G01N 2021/4757; G01N 2021/4761; G01N 2021/638; G01N 2021/6419; G01N 2021/6463; G01N 2021/6471; G01N 21/1717; G01N 21/21; G01N 21/274; G01N 21/359; G01N 21/39; G01N 21/45; G01N 21/49; G01N 21/636; G01N 21/6408; G01N 2201/06; G01N 2201/0612; G01N 2201/129; G01N 2201/1293; G01N 2800/042; G01N 2800/387; G01N 2800/7023; G01N 2800/7028; G01N 23/046
See application file for complete search history.

(56) References Cited

U.S. PATENT DOCUMENTS

| | | | |
|---|---|---|---|
| 7,447,408 B2 | 11/2008 | Bouma et al. | |
| 7,551,293 B2 | 6/2009 | Yelin et al. | |
| 7,796,270 B2 | 9/2010 | Yelin et al. | |
| 7,847,949 B2 | 12/2010 | Tearney et al. | |
| 7,859,679 B2 | 12/2010 | Bouma et al. | |
| 7,889,348 B2 | 2/2011 | Tearney et al. | |
| 8,045,177 B2 | 10/2011 | Tearney et al. | |
| 8,145,018 B2 | 3/2012 | Shishkov et al. | |
| 8,838,213 B2 | 9/2014 | Tearney et al. | |
| 8,917,390 B2 | 12/2014 | Behr et al. | |
| 9,254,089 B2 | 2/2016 | Tearney et al. | |
| 9,295,391 B1* | 3/2016 | Tearney | A61B 1/07 |
| 9,415,550 B2 | 8/2016 | Tearney et al. | |
| 9,557,154 B2 | 1/2017 | Tearney et al. | |
| 2010/0315652 A1* | 12/2010 | Yelin | G01B 9/0201 |
| | | | 356/521 |
| 2012/0101374 A1 | 4/2012 | Tearney et al. | |
| 2014/0354802 A1 | 12/2014 | Ohtomo et al. | |
| 2016/0206184 A1 | 7/2016 | Tearney et al. | |
| 2016/0341951 A1 | 11/2016 | Tearney et al. | |
| 2016/0349417 A1 | 12/2016 | Tearney et al. | |
| 2017/0035281 A1* | 2/2017 | Takeuchi | G02B 27/4227 |
| 2017/0167861 A1 | 6/2017 | Chen et al. | |
| 2017/0168232 A1 | 6/2017 | Tearney et al. | |
| 2017/0176736 A1 | 6/2017 | Yamamoto et al. | |
| 2017/0290492 A1 | 10/2017 | Hamm et al. | |
| 2017/0322079 A1 | 11/2017 | Do et al. | |
| 2018/0017806 A1* | 1/2018 | Wang | G01B 9/02044 |

FOREIGN PATENT DOCUMENTS

| | | |
|---|---|---|
| JP | 1994233198 A | 8/1994 |
| JP | 9-172568 A | 6/1997 |
| JP | 2011023203 A | 2/2011 |
| WO | 2015/116939 A1 | 8/2015 |
| WO | 2015/116951 A2 | 8/2015 |
| WO | 2017/024145 A1 | 2/2017 |
| WO | 2017/117203 A1 | 7/2017 |
| WO | 2017/139657 A1 | 8/2017 |
| WO | 2017/165511 A1 | 9/2017 |

OTHER PUBLICATIONS

Zeidan, A et al. "Miniature forward-viewing spectrally encoded endoscopic probe", Optics Letters, Aug. 15, 2014, pp. 4871-4874, vol. 39, Issue 16.

Yelin, D., et al., "Three-dimensional miniature endoscopy", Nature, Oct. 19, 2006, p. 765, vol. 443.

(56) References Cited

OTHER PUBLICATIONS

Kang, D., et al., "Minature grating for spectrally-encoded endoscopy", Lab Chip, 2013, pp. 1810-1816, vol. 13.

\* cited by examiner

IMAGE ACQUIRING APPARATUS, SYSTEMS, AND METHODS

BACKGROUND OF THE INVENTION

Field of the Invention

The present invention relates to endoscopes and, in particular, relates to a spectrometer that separates and measures an obtained light beam in accordance with the wavelengths, such as, but not limited to, spectrally encoded endoscopy (SEE) apparatuses and systems, and methods and storage mediums for use with same. Examples of SEE applications include imaging, evaluating and characterizing/identifying biological objects or tissue, such as, but not limited to, for gastro-intestinal, cardio and/or ophthalmic applications.

Description of the Related Art

Conventionally, endoscope apparatuses for use in intraluminal measurement are known. Endoscopes make it possible to observe intraluminal information in real time, and endoscopes with a smaller outer diameter can be inserted into a greater variety of lumina, leading to an increase in the observation areas.

Spectrally encoded endoscope (SEE) is an endoscope technology which uses a broadband light source, a rotating grating and a spectroscopic detector to encode spatial information on a sample. When illuminating light to the sample, the light is spectrally dispersed along one illumination line, such that the dispersed light illuminates a specific position of the illumination line with a specific wavelength. When the reflected light from the sample is detected with the spectrometer, the intensity distribution is analyzed as the reflectance along the line. By rotating or swinging the grating back and forth to scan the illumination line, a two-dimensional image of the sample is obtained.

A spectrally encoded endoscope such as the one disclosed in U.S. Pat. No. 6,341,036 is an example of a small-diameter endoscope. In the SEE device disclosed in U.S. Pat. No. 6,341,036, white light is made incident on a diffraction grating to generate a spectrum of white light, and a subject is irradiated with that spectral sequence. Only the light beams corresponding to the respective wavelengths of the spectral sequence reach the respective positions on the subject, and thus by measuring the reflectance of the spectral sequence, one-dimensional reflectance information can be obtained. By moving the reflectance information in another axial direction, a two-dimensional image can be obtained. In other words, the wavelength information is converted to the positional information, and an image is obtained from the reflectance in each piece of the positional information. However, in the technique disclosed in U.S. Pat. No. 6,341,036, an image to be obtained is a monochrome image, and a color image cannot be obtained.

U.S. Pat. No. 9,254,089 proposed a technique for obtaining a color image in SEE. U.S. Pat. No. 9,254,089 describes the following technique. Specifically, three light beams at different wavelengths are guided by the respective fibers to be incident on a single diffraction grating at mutually different angles, and white illumination light is generated to obtain a color image.

However, when the technique of U.S. Pat. No. 9,254,089 is used, three mechanisms that rotatively connect to the respective fibers become necessary, which makes the mechanisms complex. In addition, the three fibers are bundled together for use, which leads to shortcomings in that the fiber portion becomes thick.

In addition, for obtaining an image, reflected light of the white illumination light is taken in, and spectrometry is carried out by using a spectrometer for computing the reflectance at each wavelength. When a spectrometer that includes a single diffraction grating and a single imaging system is assumed, the wavelength bands corresponding to red, green, and blue have distributions such that the resolution of the image is primarily associated with the resolution in the wavelength band of substantially green. Such an association with the substantially green wavelength band is due to the dependence on the sensitivity of human eyes. While a final image resolution increases as the resolution of green is increased, the resolution of green, however, on the detector in the spectrometer decreases, and it, therefore, becomes difficult to improve the resolution.

Accordingly, it would be desirable to provide at least one SEE technique, storage medium, and/or apparatus or system for use in at least one optical device, assembly or system to achieve efficient and improved resolution of an image, including in at least one embodiment a color image, of biological object(s) or tissue, especially in a way that reduces or minimizes cost of manufacture and maintenance.

SUMMARY OF THE INVENTION

Accordingly, it is a broad object of the present disclosure to provide SEE apparatuses, systems, methods, and storage mediums for use with same.

In at least one embodiment, a two-dimensional image acquiring apparatus may include: a Spectrally Encoded Endoscopy ("SEE") probe including at least one diffractive grating or element and one or more optical fibers, the at least one diffractive grating or element operating to separate and diffract a transmitted light into a plurality of separated light beams of different orders such that the diffracted light beams are overlapped or superposed or substantially overlapped or substantially superposed on a target region; at least one image sensor or detector that operates to acquire one or more intensities from a detected light; and at least one imaging optical system that operates to image a plurality of light beams separated from the detected light, wherein the at least one diffractive grating or element, the at least one imaging optical system, and the at least one image sensor or detector are disposed for each of the plurality of light beams separated from the detected light to acquire spectral data of each of the plurality of light beams separated from the detected light, and wherein the at least one diffractive grating or element operates to rotate such that an image of the at least one image sensor or detector is changed, and a two-dimensional image is acquired from the image.

The apparatus may include a light source that operates to transmit the transmitted light to the SEE probe via at least one of the one or more optical fibers such that: (i) the at least one diffractive grating or element is irradiated with the transmitted light; (ii) a sample or a target located in the target region is irradiated with the superposed or substantially superposed diffracted light beams; and (iii) reflected scattered light from the sample or the target is detected by the at least one image sensor or detector. The light source may be a supercontinuum (SC) light source having a wavelength band from blue to infrared.

In one or more embodiments, the at least one image sensor or detector comprises first and second image sensors or detectors, the at least one imaging optical system comprises first and second imaging optical systems connected or adjacent to the first and second image sensors or detectors, respectively, such that the one or more intensities from the detected light are converted by the first and second image sensors or detectors into first and second electric signals. The apparatus may further include: at least one of: (i) at least one processor that operates to receive the first and second electric signals and to generate the two-dimensional image; and (ii) a display or a screen that operates to display the generated, two-dimensional image. The apparatus may further include a spectrometer that includes the first and second image sensors or detectors, the first and second imaging optical systems, at least one color or wavelength separator that operates to separate the detected, transmitted light in accordance with one or more wavelengths into the plurality of separated light beams, a first diffraction grating and a second diffraction grating such that: (i) the first imaging optical system is disposed between the first diffraction grating and the first image sensor or detector and the second imaging optical system is disposed between the second diffraction grating and the second image sensor or detector; and (ii) the at least one color or wavelength separator is located in between or adjacent to the first diffraction grating and the second diffraction grating.

In one or more embodiments, an image acquiring apparatus may further include at least one of: (i) a spacer element disposed at a distal end of the SEE probe such that the spacer element and the at least one diffractive grating or element are adjacent and/or connected; (ii) a gradient-index lens disposed in the SEE probe adjacent or connected to the spacer element; (iii) a motor and/or a rotary junction that operates to rotate to the SEE probe; (iv) a motion control component that operates to change a speed of the motor and/or the rotary junction; and (v) a sheath housing the SEE probe.

An image acquiring apparatus may further include at least one color or wavelength separator that operates to separate the transmitted light in accordance with one or more wavelengths into the plurality of separated light beams, wherein at least one of: (i) when the two-dimensional image is generated, the at least one color or wavelength separator carries out color separation in a wavelength band in which an efficiency of the at least one diffractive grating or element is lower than that in a wavelength band used to generate the two-dimensional image on a basis of a diffraction efficiency of the at least one diffractive grating or element, (ii) the wavelength band separated by the at least one color or wavelength separator is between a wavelength band corresponding to a red signal and a wavelength band corresponding to a green signal in a color image, and (iii) the at least one color or wavelength separator is a dichroic mirror. An image sensor may be disposed in the vicinity of a focal point of the image sensor.

In one or more embodiments, one or more of the following conditions may be included: (i) the at least one image sensor or detector includes two image sensors, the two image sensors being an image sensor configured to acquire spectral data corresponding to a red signal in a color image and an image sensor configured to acquire spectral data corresponding to blue and green signals, respectively; (ii) the at least one diffractive grating or element includes two diffractive elements, the two diffractive elements being a diffractive element configured to separate a wavelength band corresponding to a red signal in a color image and a diffractive element configured to separate a wavelength band corresponding to blue and green signals, respectively; and (iii) the at least one imaging optical system includes two imaging optical systems, the two imaging optical systems being an imaging optical system configured to image a wavelength band corresponding to a red signal in a color image and an imaging optical system configured to image a wavelength band corresponding to blue and green signals, respectively. In one or more embodiments, a wavelength band corresponding to the red signal is no less than about 600 nm nor more than about 900 nm, and the wavelength band corresponding to the blue and green signals is no less than about 400 nm nor more than about 600 nm.

The image acquiring apparatus may be an endoscope apparatus in one or more embodiments.

The one or more optical fibers may include: (i) one or more illumination fibers that operate to send light from a light source to the grating to illuminate the target region with light; and (ii) one or more detection fibers that operate to receive light reflected from a target or a sample disposed in the target region and that passes back through the grating and into the one or more detection fibers.

In accordance with another aspect of the present disclosure, a two-dimensional image acquiring apparatus may include: a Spectrally Encoded Endoscopy ("SEE") probe including a first grating and one or more optical fibers, the first grating operating to separate and diffract a light transmitted via a first optical fiber of the one or more optical fibers into a plurality of separated light beams of different orders such that the diffracted light beams are overlapped or superposed or substantially overlapped or substantially superposed on a target region, the one or more optical fibers including a second optical fiber that operates to transmit detected light from the target region on which the diffracted light is incident; a wavelength or color separator to separate the light transmitted by the second optical fiber, in accordance with a wavelength into at least two beams of light including a first light beam and a second light beam; for each light beam, the image acquiring apparatus may further include: a second grating to diffract a corresponding one of the at least two beams; imaging optics to receive the light diffracted by the second grating, and to provide an image; and an image pickup device arranged at or around a focal point of the imaging optics, wherein a two-dimensional image is obtained from images acquired, while the first grating is rotated, by the image pickup device, wherein the wavelength or color separator separates the transmitted light between a first band of wavelength corresponding to a red signal and a second band of wavelength corresponding to blue and green signals or to a green signal.

In accordance with yet another aspect of the present disclosure, a two-dimensional image acquiring apparatus may include: a light source; a diffractive element, light from the light source being transmitted via a fiber, the diffractive element being irradiated with the transmitted light, a target or subject being irradiated with a light beam separated by the diffractive element in accordance with a wavelength, reflected scattered light from the target or subject being transmitted via a fiber, the diffractive element separating the reflected scattered, transmitted light in accordance with a wavelength; an imaging optical system configured to image the separated light beam; and an image sensor disposed in the vicinity of a focal point of the image sensor, wherein the diffractive element is rotated so as to change an image of the image sensor, and a two-dimensional image is acquired from the image, wherein a wavelength or color separator configured to separate the reflected scattered, transmitted light in accordance with a wavelength is provided, wherein the diffractive element, the imaging optical system, and the image sensor are disposed for each of the light beams separated from the reflected scattered, transmitted light to thus acquire spectral data of each of the light beams separated from the reflected scattered, transmitted light, and wherein the wavelength band separated by the wavelength or color separator is between a wavelength band corresponding to a red signal and a wavelength band corresponding to a blue-green signal or a green signal in a color image.

In accordance with an even further aspect of the present disclosure, a method for controlling a two-dimensional image acquiring apparatus may include: defining a spectrum of wavelength ranges to use for acquiring the two-dimensional image such that the spectrum bands overlap or substantially overlap on a sample or target; detecting light reflected from the sample or target; separating the detected light into two or more light beams having different wavelengths or colors using a wavelength or color separator of a spectrometer having a cut-off wavelength set to be out of the defined wavelength ranges; and imaging the light beams separated from the detected light to acquire or generate the two-dimensional image. The method may further include using a probe grating to generate the spectrum bands that overlap or substantially overlap on the sample or target. One or more methods may further include optimizing the probe grating so that a diffraction efficiency is high within the wavelength ranges.

In accordance with yet an even further aspect of the present disclosure, a computer-readable storage medium may be provided, the medium storing at least one program that operates to cause one or more processors to execute one or more of the methods discussed herein.

At least one additional aspect of the present disclosure provides a two-dimensional image acquiring apparatus that includes a light source; a diffractive element, light from the light source being transmitted via a fiber, the diffractive element being irradiated with the transmitted light, a subject being irradiated with a light beam separated by the diffractive element in accordance with a wavelength, reflected scattered light from the subject being transmitted via a fiber, the diffractive element again separating the transmitted light in accordance with a wavelength; an imaging optical system configured to image the separated light beam; and an image sensor disposed in the vicinity of a focal point of the image sensor. The diffractive element is rotated so as to change an image of the image sensor, and a two-dimensional image is acquired from the image. A color separation unit configured to separate the transmitted light in accordance with a wavelength is provided. The diffractive element, the imaging optical system, and the image sensor are disposed for each of the separated light beams to thus acquire spectral data of each of the separated light beams. The light beam separated by the diffractive element is diffracted such that diffracted light beams of different orders of diffraction are superposed on a given region. When the two-dimensional image is generated in at least one embodiment, the color separation unit carries out color separation in a wavelength band in which an efficiency of the diffractive element is lower than that in a wavelength band used to generate the two-dimensional image on a basis of a diffraction efficiency of the diffractive element. In one or more embodiments, (i) a spectrum of wavelength ranges is defined to use for imaging (e.g., for R,G,B spectrum bands) such that spectrum bands (e.g., for R,G,B colors) overlap (e.g., are superposed or substantially superposed) on a target; (ii) a probe grating is optimized so that a diffraction efficiency is high within the wavelength ranges; and (iii) a beam splitter cut-off wavelength of a spectrometer is set to be out of the defined wavelength ranges.

For obtaining a color image in SEE, by using higher-order diffracted light of a diffraction grating disposed at a leading end, white illumination light is generated by superposing diffracted light beams in red, green, and blue regions with different orders of diffraction. In addition, the acquisition wavelength band of a detection spectrometer is divided, and the divided region is set to a band in which the diffraction efficiency of the diffraction grating disposed on the probe side is low. Thus, the resolution of an acquired image can be improved without degrading the utilization efficiency of the acquired light.

In accordance with at least another aspect of the present disclosure, the SEE technique(s) discussed herein may be employed to reduce the cost of at least one of manufacture and maintenance of SEE devices, systems and storage mediums by reducing or minimizing a number of optical components in an interference optical system, such as an interferometer.

In accordance with at least a further aspect of the present disclosure, the SEE technique(s) discussed herein may be used in or used with an interference optical system, such as an interferometer.

According to other aspects of the present disclosure, one or more additional apparatuses, one or more systems, one or more methods, and one or more storage mediums using SEE technique(s) are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE EMBODIMENTS

One or more devices, optical systems, methods, and storage mediums for improving resolution of an image of a subject, such as tissue, using a SEE technique and/or for obtaining a color image using a SEE technique are disclosed herein. In accordance with at least one aspect of the present disclosure, one or more devices, optical systems, methods, and storage mediums discussed herein use a SEE technique to improve image resolution and/or to obtain images in color while improving the resolution.

Figure 1A:
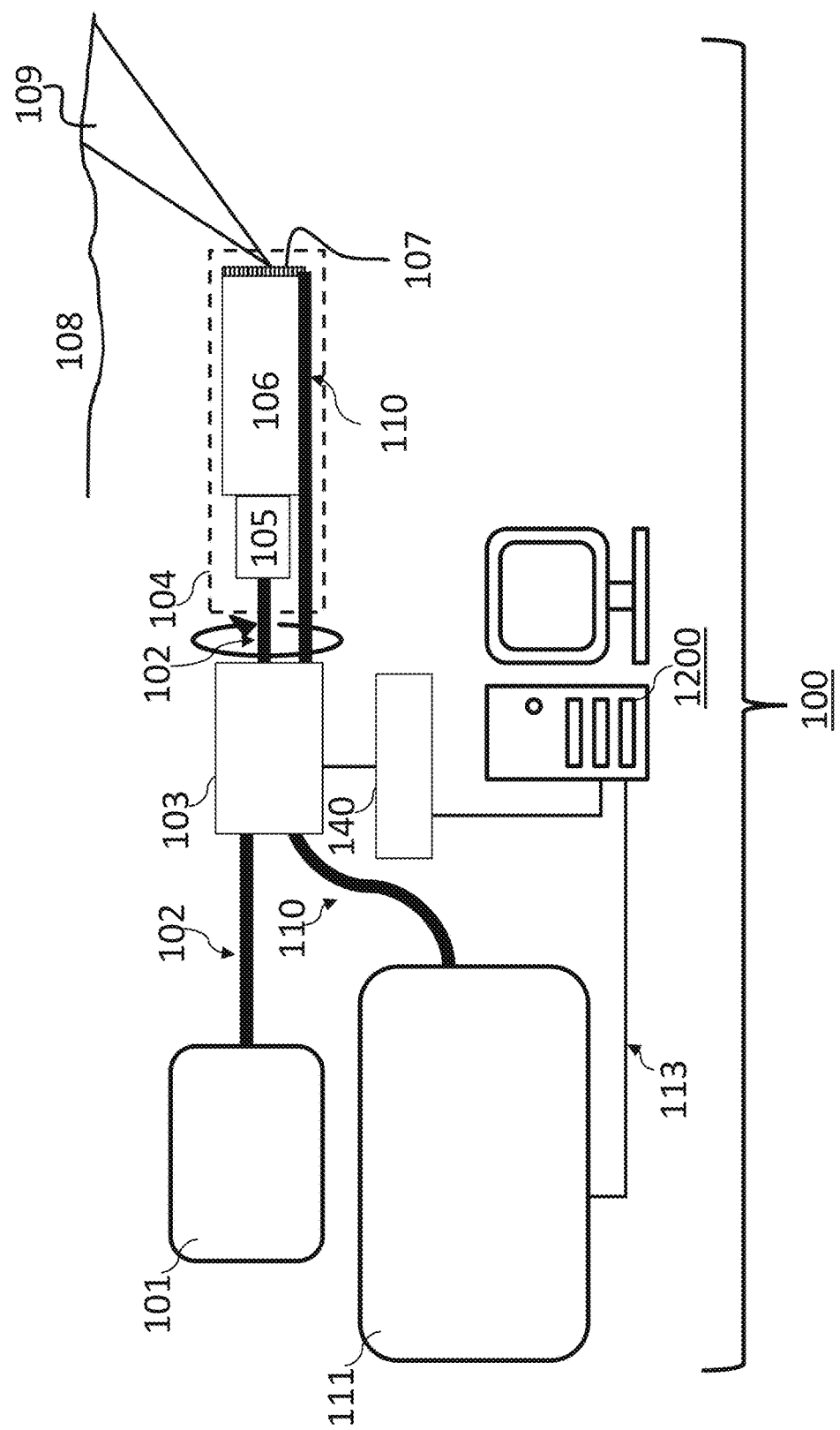
FIG. 1A is a system diagram of a SEE system according to at least a first embodiment in accordance with one or more aspects of the present disclosure.
Figure 1B:
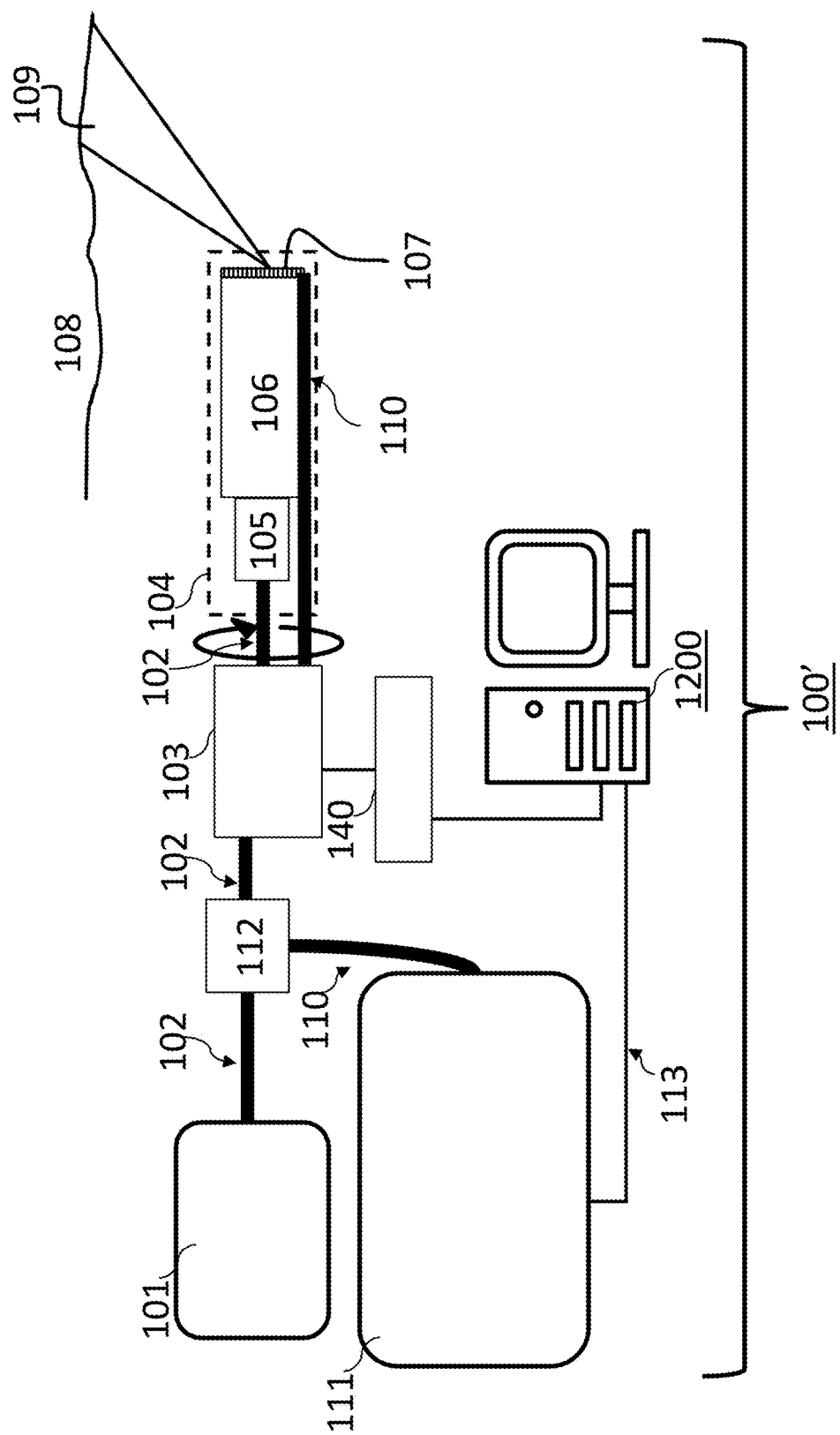
FIG. 1B is a system diagram of a SEE system according to at least a further embodiment in accordance with one or more aspects of the present disclosure.
Figure 2:
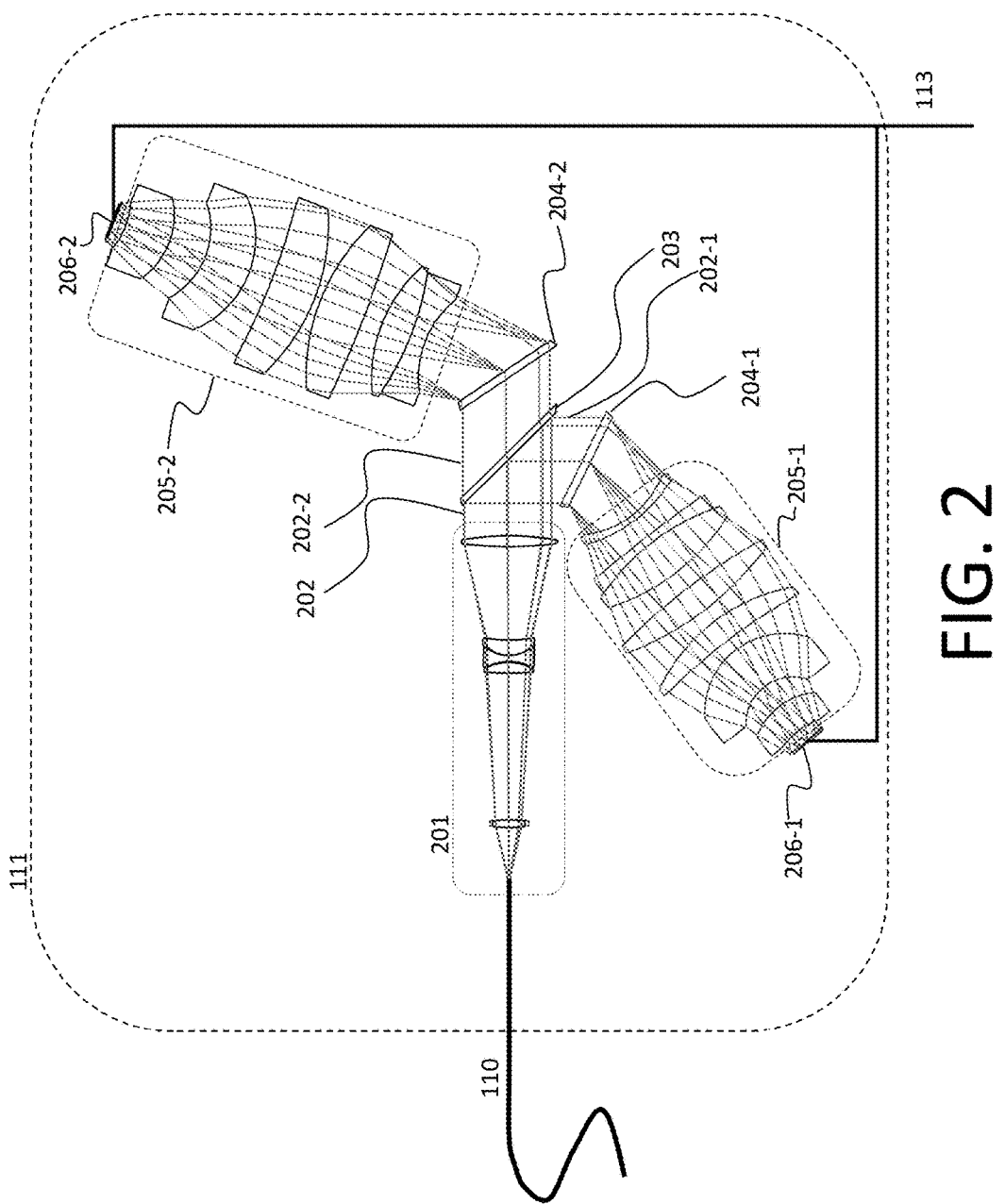
FIG. 2 is an optical sectional view of a spectrometer illustrated in at least FIGS. 1A and 1B.
Figure 3:
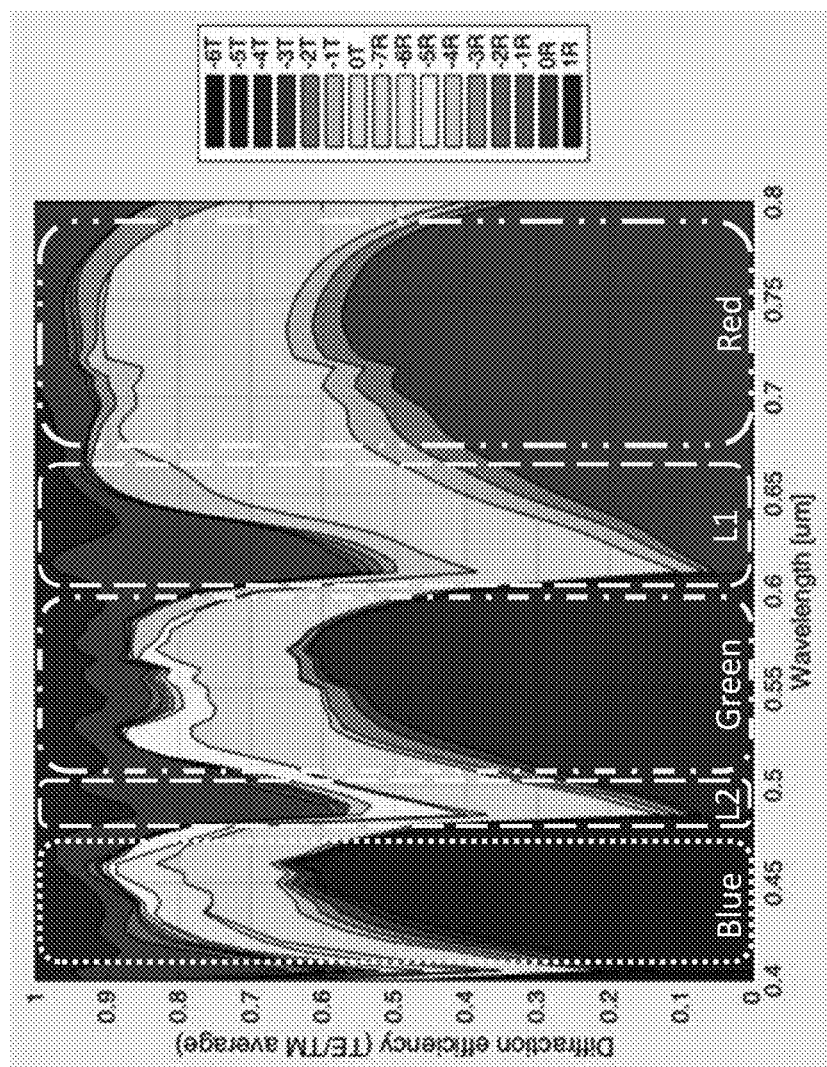
FIG. 3 illustrates the diffraction efficiency of a diffractive element disposed at a probe portion according to at least the first embodiment in accordance with one or more aspects of the present disclosure.
Figure 4:
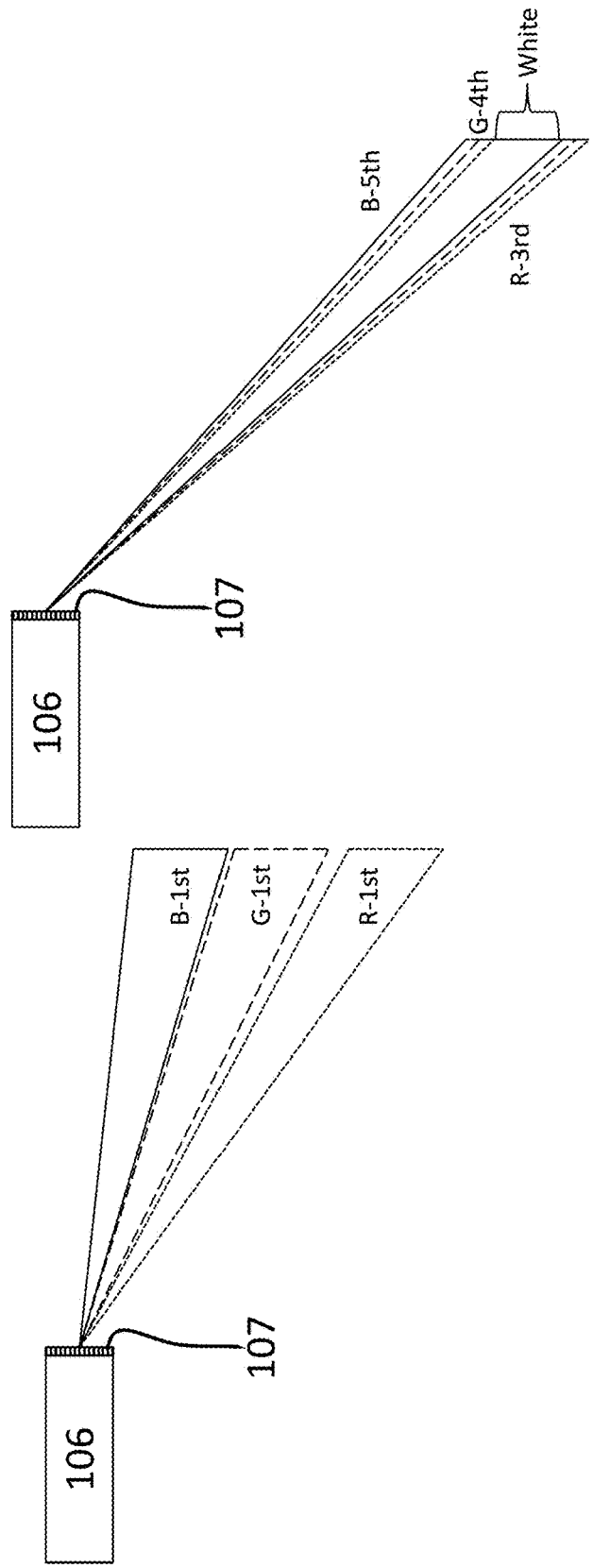
FIGS. 4A and 4B are schematic diagrams for describing white light illumination formed by the diffractive element according to at least the first embodiment in accordance with one or more aspects of the present disclosure.
Figure 5:
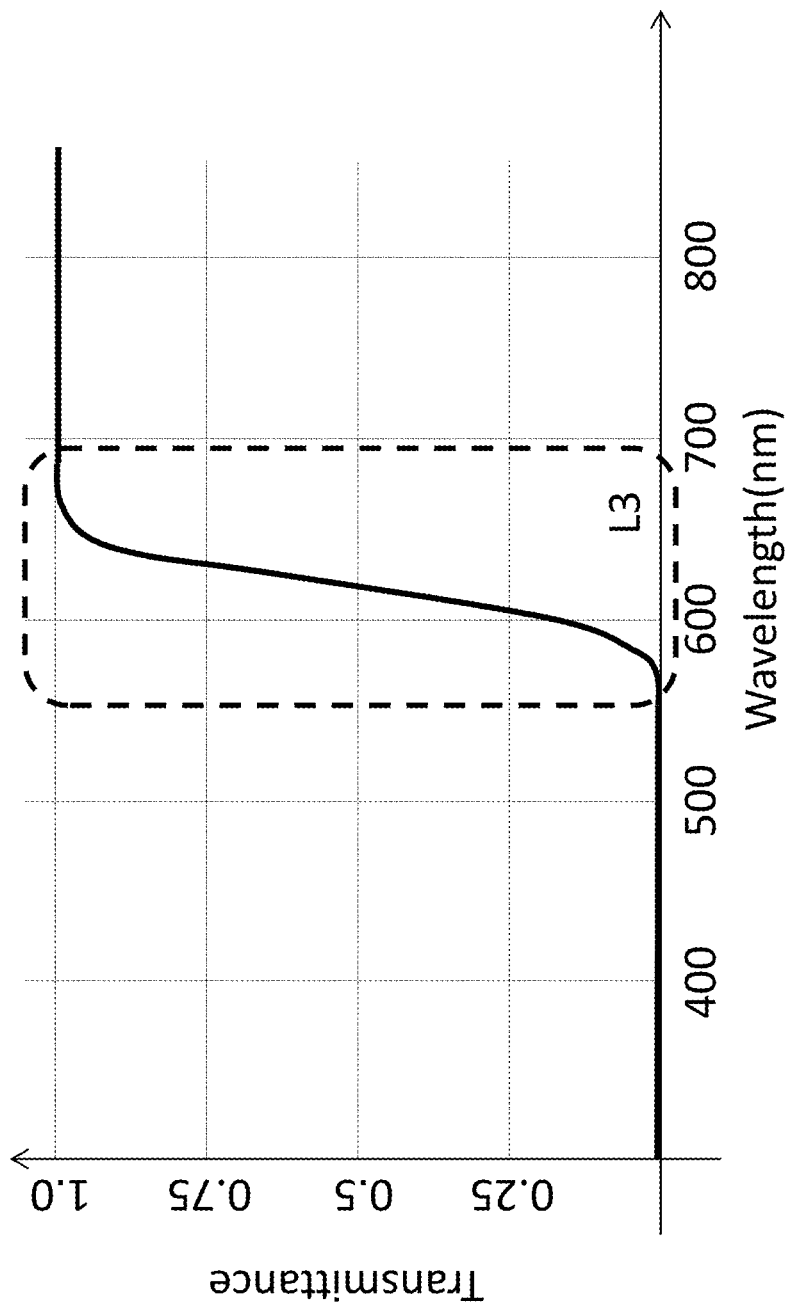
FIG. 5 illustrates the wavelength characteristics of a dichroic mirror according to at least the first embodiment in accordance with one or more aspects of the present disclosure.

With reference to FIGS. 1A to 5, a first embodiment of the present disclosure is described herein (with a further or alternative embodiment being shown in FIG. 1B as discussed below). FIGS. 1A and 1B illustrate respective overall SEE systems including a spectrometer according to the present, respective embodiments, and FIG. 2 illustrates an optical section of the spectrometer disposed in the SEE system of FIGS. 1A and 1n the SEE system of FIG. 1B. FIG. 1B illustrates the overall SEE system including a spectrometer as shown in FIG. 1A (see e.g., system 100), with the exception being that a deflecting or deflected section 112 is incorporated into the system 100' of FIG. 1B such that the cable or fiber 102 connecting the light source 101 to the rotary junction 103 and/or the probe section 104 and the cable or fiber 110 connecting the spectrometer 111 to the rotary junction 103 and/or the probe section 104 pass through, and are connected via, the deflected section 112 (discussed further below). FIG. 3 illustrates the diffraction efficiency of a diffractive element at a probe portion according to the present embodiment(s), FIGS. 4A and 4B illustrate how white illumination light is formed by the diffractive element, and FIG. 5 illustrates an example of the wavelength characteristics of a dichroic mirror disposed in the spectrometer.

As shown in FIG. 1A, light emitted by a white light source 101 is transmitted by an illumination light transmission fiber 102 and is incident on a probe portion 104 (also referred to herein as "probe section 104") via a rotary junction (hereinafter, RJ) 103 (e.g., the fiber 102 may extend through the RJ 103 and into the probe portion 104). Additionally or alternatively, the light emitted by the white light source 101 may be transmitted by the illumination light transmission fiber 102 and is incident on the probe portion 104 via a deflecting or deflected section 112 and via the RJ 103. In one or more embodiments of the probe portion 104, the white light beam is incident on a spacer 106 via a gradient-index lens (hereinafter, GRIN lens) 105. A diffraction grating (hereinafter, diffractive element) 107 is provided at the leading end portion of the spacer 106 (e.g., the GRIN lens 105 and the diffraction grating 107 are located on opposite sides of the spacer 106), and as the white light beam is incident on this diffractive element 107, a spectral sequence 109 is formed on a subject 108. In one or more embodiments, the probe portion 104 may not include the spacer 106, and the GRIN lens 105 may be connected to the diffractive element 107 to permit the spectral sequence 109 to be formed on the subject 108. Reflected light from the spectral sequence 109 (e.g., light from the spectral sequence 109 that is formed on, and is reflected by, the subject 108; light that is reflected by the subject 108; etc.) is taken in by a detection fiber or cable 110. Although one detection fiber 110 is illustrated in FIG. 1A and in FIG. 1B, a plurality of detection fibers may be used. In one or more embodiments, the detection fiber 110 may extend to and/or near the end of the probe section 104. For example, in the system 100 of FIG. 1A and in the system 100' of FIG. 1B, the detection fiber 110 may have a detection fiber portion (see fiber 110 extending through the probe portion 104 in each of FIGS. 1A and 1B) that extends from or through the RJ 103 through, and to and/or near (e.g., adjacent to the end of the probe section 104, about the end of the probe portion 104, near the end of the probe portion 104 closest to the sample 108, etc.) the end of, the probe section 104 (see also, FIG. 8 which diagrammatically shows the detection fiber 110 in such a configuration as discussed below). The light taken in by the detection fiber 110 is separated into spectral components and detected by at least one detector, such as, but not limited to, a spectrometer 111 (and/or one or more components thereof as discussed herein), provided at the exit side of the detection fiber 110. In one or more embodiments, the end of the detection fiber 110 that takes in the reflected light may be disposed on or located near at least one of: the diffraction grating 107, the end of the spacer 106, the end of the probe portion 104, etc. Additionally or alternatively, the reflected light may be passed at least one of: through the probe portion 104, through the GRIN lens 105, through the rotary junction 103, etc., and the reflected light may be passed, via a deflecting or deflected section 112 (discussed below), to the spectrometer 111. As shown in FIGS. 1A and 1B, as the portion extending from the RJ 103 to the probe portion 104 is rotated about the rotational axis extending in the longitudinal direction of the probe portion 104, the spectral sequence 109 moves in a direction orthogonal to the spectral sequence 109, and reflectance information in two-dimensional directions may be obtained. Arraying these pieces (e.g., the reflectance information in two-dimensional directions) of information makes it possible to obtain a two-dimensional image.

Preferably, in one or more embodiments including the deflecting or deflected section 112 (best seen in FIG. 1B), the deflected section 112 operates to deflect the light from the light source 101 to the probe portion 104, and then send light received from the probe portion 104 towards at least one detector (e.g., the spectrometer 111, one or more components of the spectrometer such as the detectors 206-1 and 206-2 of the spectrometer 111 (as shown in FIG. 2), etc.). In one or more embodiments, the deflected section (e.g., the deflected section 112 of the system 100' as shown in FIG. 1B) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100 or of the system 100', such as, but not limited to, one or more of the light source 101, the deflected section 112, the rotary junction 103, and/or the probe portion 104 (and/or one or more components thereof).

FIG. 2 is an optical sectional view of the spectrometer 111 (e.g., of the system 100 of FIG. 1A, of the system 100' of FIG. 1B, etc.). The light beam that has exited from a fiber end of the detection fiber 110 is converted into a parallel light beam 202 by a collimator 201, and the parallel light beam 202 is incident on a dichroic mirror 203. The parallel light beam 202 is split into light beams 202-1 and 202-2 in two wavelength bands by the dichroic mirror 203, and the light beams 202-1 and 202-2 are incident on diffraction gratings 204-1 and 204-2, respectively. Upon having been diffracted by the diffraction gratings 204-1 and 204-2, the light beams 202-1 and 202-2 are imaged by imaging optical systems 205-1 and 205-2, respectively, converted into electric signals by one-dimensional image sensors 206-1 and 206-2, respectively, and thus converted into intensity information at respective wavelengths. The electric signals may be sent to one or more processors, such as, but not limited to, a computer 1200 (see e.g., FIGS. 1A-1B), a computer 1200', or a processing circuit 801 as discussed further below, via cable(s) or wire(s), such as, but not limited to, the cable(s) or wire(s) 113 (see FIGS. 1A-1B). By detecting this intensity information temporally in accordance with the movement of the spectral sequence 109, a two-dimensional image may be obtained.

In at least one embodiment, the console or computer 1200, 1200' operates to control motions of the RJ 103 via a Motion Control Unit (MCU) 140, acquires intensity data from the detector(s) (e.g., the detectors 206-1 and 206-2) in the spectrometer 111, and displays the scanned image (e.g., on a monitor or screen such as a display, screen or monitor 1209 as shown in the console 1200 of FIG. 10 and/or the console 1200' of FIG. 11 as further discussed below). In one or more embodiments, the MCU 140 operates to change a speed of a motor of the RJ 103 and/or of the RJ 103. The motor may be a stepping or a DC servo motor to control the speed and increase position accuracy.

The diffractive element 107 provided on the spacer 106 will be described with reference to FIGS. 3, 4A and 4B.

Typically, when white light is incident on a diffraction grating, a rainbow-colored spectral sequence is formed by a first-order diffracted light. In SEE, illumination of such first-order diffracted light does not raise any issues when a monochrome image is to be acquired. However, when a color image is to be acquired, reflectance information corresponding to the three primary colors of red, green, and blue from the same position on a subject is necessary in one or more embodiments. In the method in which first-order diffracted light alone is used, reflected light from a given portion of a subject contains information only on a single wavelength (FIG. 4A). Thus, with one or more methods in which first-order diffracted light alone is used, another method becomes necessary for acquiring a color image.

Thus, as illustrated in FIG. 4B, higher-order diffracted light is used in one or more embodiments. With respect to diffraction, the angle of diffraction is greater as the wavelength is longer. In addition, higher-order diffracted light has a greater angle of diffraction. By using the above, for example, fifth-order diffracted light is used in blue (short wavelength), fourth-order diffracted light is used in green (mid wavelength), and third-order diffracted light is used in red (long wavelength) (see FIG. 4B). At this point, by selecting the pitch of the diffractive element 107 appropriately, light beams can be diffracted so that the third-order diffracted light, the fourth-order diffracted light, and the fifth-order diffracted light are substantially superposed on one another on the subject. With such configurations, a blue spectral sequence, a green spectral sequence, and a red spectral sequence can be superposed or substantially superposed on the subject to form illumination light of a spectral sequence corresponding to white light.

When higher-order diffracted light is used, an issue that arises is the diffraction efficiency. When an amplitude-type diffractive element is used as the diffractive element 107, the first-order diffracted light has the highest diffraction efficiency, and the diffraction efficiency decreases as the order of diffraction increases. In contrast, when a phase-type diffraction grating is used, the diffraction efficiency of higher-order diffracted light can be improved by appropriately selecting the grating height of the diffraction grating and the refractive index of the base material. For example, when a phase-type diffraction grating such as the one summarized in Table 1 is used as the diffractive element 107, the grating height and the refractive index may be set such that the fifth-order diffracted light may achieve, in one or more embodiments, the highest efficiency at around 408 nm to 468 nm, the fourth-order diffracted light may achieve the highest efficiency at around 510 nm to 585 nm, and third-order diffracted light may achieve the highest efficiency at around 680 nm to 780 nm, as illustrated in FIG. 3. By using a diffraction grating of such a shape as the diffractive element 107, a spectral sequence that results in white light on a subject can be obtained.

TABLE 1

Parameters of the diffractive element 107 according to at least a first embodiment

| | Diffractive Element 107 |
|---|---|
| pitch (μm) | 1.25 |
| duty cycle | 0.8 |
| depth (μm) | 1.7 |
| refractive index | 1.50 |

The reflectance information obtained in this manner may be converted into the intensity information by the spectrometer 111 and is turned into an image. Here, a color image may be obtained by superposing or substantially superposing the pieces of intensity information corresponding to the three primary colors of red, green, and blue. The resolution of the color image is dependent on the wavelength resolving power of red, green, and blue by the spectrometer 111, and the resolution increases as the wavelength resolving power is higher. However, when there is only a single diffraction grating within a spectrometer, the following issues may arise.

Human eyes are sensitive to the resolution in the wavelength band corresponding to green and perceive as a higher-resolution image when the resolution of green, among red, blue, and green, is higher. However, when the optical system extending from a diffraction grating (e.g., the diffraction grating 204-1, the diffraction grating 204-2, etc.) to the image sensor (e.g., the image sensor 206-1, the image sensor 206-2, respectively, etc.) within the spectrometer 111 is constituted by a single optical system, the red region appears larger on the image sensor due to the physical characteristics of diffraction. As a result, the resolution of red becomes the highest, and the resolution of green is greatly lower than that of red.

When higher-order diffracted light is used, a region in which the diffraction efficiency is very low appears between the regions corresponding to blue, green, and red in which the diffraction efficiency is high (region L1 in FIG. 3). In at least one embodiment, a region in which the diffraction efficiency is low is a region in which the diffraction efficiency is equal to or less than a half of the highest diffraction efficiency in each of the regions of blue, green, and red. When the optical system extending from a diffraction grating 204 (e.g., the diffraction grating 204-1, the diffraction grating 204-2, etc.) to a respective image sensor 206 (e.g., the image sensor 206-1, the image sensor 206-2, respectively, etc.) within the spectrometer 111 is constituted by a single optical system, the region on the image sensor corresponding to the aforementioned region results in a very dark image. Thus, the pixels in this region result in wasted pixels, leading to a decrease in the final resolution.

To address the issues described above, the portion extending from the diffraction grating (e.g., the diffraction grating 204-1, the diffraction grating 204-2, etc.) to the image sensor (e.g., the image sensor 206-1, the image sensor 206-2, respectively, etc.) is separated into two in accordance with the wavelength band, as illustrated in FIG. 2, in one or more embodiments of the present disclosure. In at least one embodiment, the separation wavelength band of the dichroic mirror (region L3 in FIG. 5) is set to a wavelength band in which the diffraction efficiency is low in the diffractive element 107.

With this configuration, the resolution corresponding, in particular, to green may be improved due to the following two effects, and a high-resolution image may be obtained. Specifically, the resolution of the image may be improved by selecting an appropriate diffraction grating (e.g., the diffraction grating 204-1, the diffraction grating 204-2, etc.) for each wavelength band and by selecting an optimal angle of diffraction suitable for the image sensor (e.g., the image sensor 206-1, the image sensor 206-2, respectively, etc.). The resolution may be improved by setting a region in which the diffraction efficiency is low as a region that does not contribute to forming the image and by reducing the wasted pixels on the image sensor (e.g., the image sensor 206-1, the image sensor 206-2, respectively, etc.) as much as possible. Table 2 summarizes parameters of the diffraction gratings 204-1 and 204-2 used in at least the present embodiment.

TABLE 2

Parameters of the diffraction gratings 204-1 and 204-2
in at least one embodiment of the present disclosure

|  | 204-1 | 204-2 |
|---|---|---|
| pitch (μm) | 0.571 | 0.625 |

Here, the one-dimensional image sensors 206-1 and 206-2 have the same specifications. With this configuration, the image sensors and the processing circuits and so on associated with the image sensors can be made uniform. In addition, when the image sensors are made uniform, the pitch of the diffraction grating 204-1 that separates the blue and green light is made finer than the pitch of the diffraction grating 204-2 that separates the red light. With this configuration, the blue and green light, which is the light on the shorter wavelength side, that has a smaller angle of diffraction may be diffracted at a greater angle, and the resolution of green may be increased.

For one or more embodiments, the expression the diffraction efficiency is "low" means that the diffraction efficiency is lower than the value of the highest diffraction efficiency at each order of diffraction. For example, in one or more embodiments, it is desirable that the diffraction efficiency be lower than the value at the peak of the diffraction efficiency by approximately 50% or more. In one or more embodiments, it is preferably that the following conditions are met: (i) a spectrum of wavelength ranges is defined to use for imaging (e.g., for R,G,B spectrum bands) such that spectrum bands (e.g., for R,G,B colors) overlap (e.g., are superposed or substantially superposed) on a target; (ii) a probe grating is optimized so that a diffraction efficiency is high within the wavelength ranges; and (iii) a beam splitter cut-off wavelength of a spectrometer is set to be out of the defined wavelength ranges.

In addition, in the spectrometer according to at least the present embodiment, while the wavelength range corresponding to blue to green may be set to 408 nm to 585 nm, and while the wavelength range corresponding to red may be set to 680 nm to 780 nm, the ranges are not limited thereto. When a spectrometer (e.g., the spectrometer 111) for use in SEE is assumed, it is desirable that the wavelength range of blue to green be equal to about or exceeds 400 nm on the shorter wavelength side. The reason for this is as follows. In one or more embodiments, a sufficient signal cannot be obtained in a wavelength range shorter than 400 nm because the transmittance of a material used for the optical system becomes lower at a shorter wavelength. Furthermore, when the wavelength exceeds 405 nm, higher transmittance may be obtained, which is thus desirable. In addition, it is desirable that the wavelength range for blue to green on the longer wavelength side fall at or below 600 nm. The reason for this is as follows. When the spectrometer (e.g., the spectrometer 111) is used as a device for observing a biological tissue, it is highly likely that an appropriate reflection image cannot be obtained because the absorption spectrum of hemoglobin present in a large amount within a body changes sharply around 600 nm. To be more specific, it is desirable that the wavelength fall at about or below 590 nm in at least one embodiment. With this configuration, a more accurate reflection image may be obtained. In addition, it is desirable that the lower limit of the wavelength range for red be longer than 600 nm for the same reason as that for the upper limit of blue to green. To be more specific, it is desirable that the stated lower limit be about or exceeds 620 nm in at least one embodiment. In addition, it is desirable that the upper limit be about or falls below 900 nm. The reason for this is as follows. When the upper limit wavelength is longer than 900 nm, if the sufficient sensitivity is provided in the visible-light band in an Si-based sensor that is typically used as an image sensor, the sensitivity decreases at a wavelength of 900 nm or longer. To be more specific, when the upper limit falls below 850 nm in at least one embodiment, a higher sensitivity may be obtained as a whole.

In this manner, the resolution of an obtained color image may be improved in one or more situations by making the wavelength band in which the diffraction efficiency of the diffractive element at the probe portion is low (i.e., "low" means that the diffraction efficiency is lower than the value of the highest diffraction efficiency at each order of diffraction. In at least one embodiment, the diffraction efficiency is low when the diffraction efficiency is lower than the value at the peak of the diffraction efficiency by approximately 50% or more) coincide with the separation wavelength band of the spectrometer in the configuration of SEE that obtains a color image with the use of higher-order diffracted light. As also aforementioned, in one or more embodiments, it is preferably that the following conditions are met: (i) a spectrum of wavelength ranges is defined to use for imaging (e.g., for R,G,B spectrum bands) such that spectrum bands (e.g., for R,G,B colors) overlap (e.g., are superposed or substantially superposed) on a target; (ii) a probe grating is optimized so that a diffraction efficiency is high within the wavelength ranges; and (iii) a beam splitter cut-off wavelength of a spectrometer is set to be out of the defined wavelength ranges.

Figure 6:
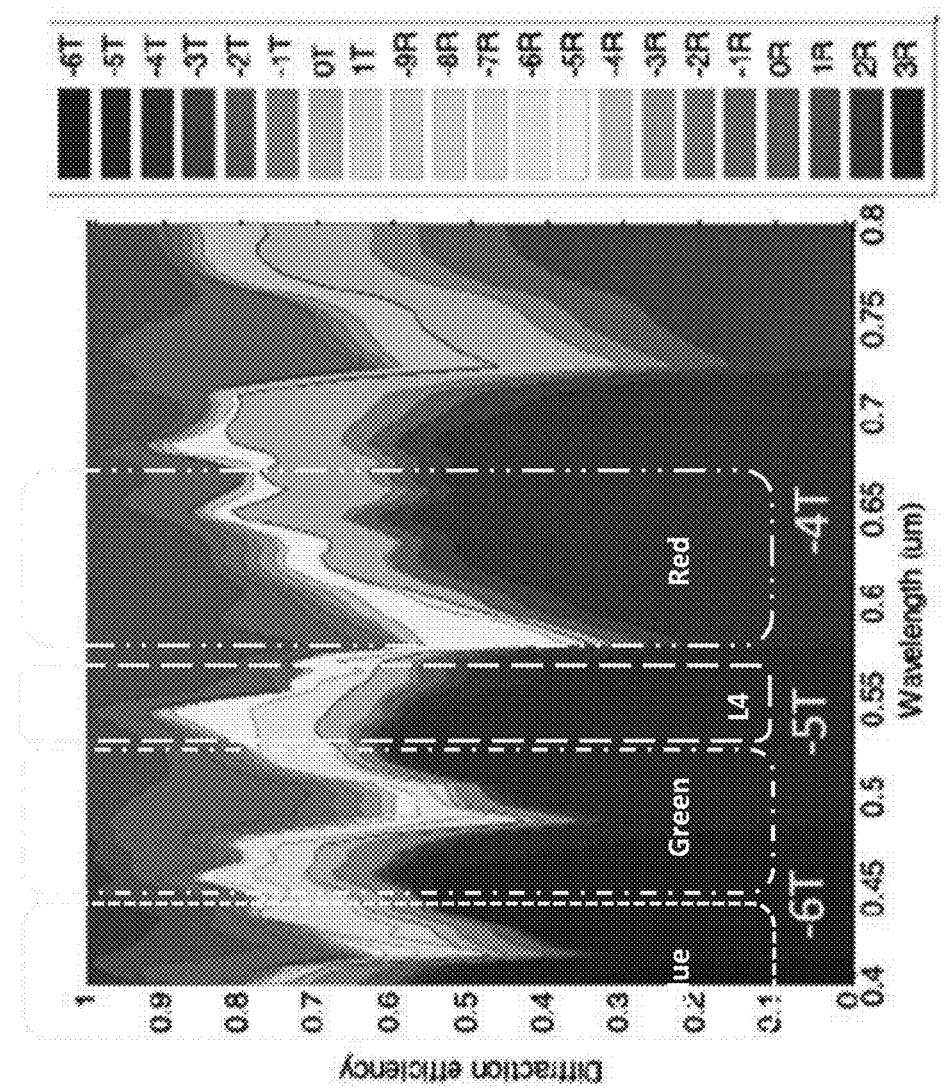
FIG. 6 illustrates the diffraction efficiency of a diffractive element according to at least a second embodiment in accordance with one or more aspects of the present disclosure.
Figure 7:
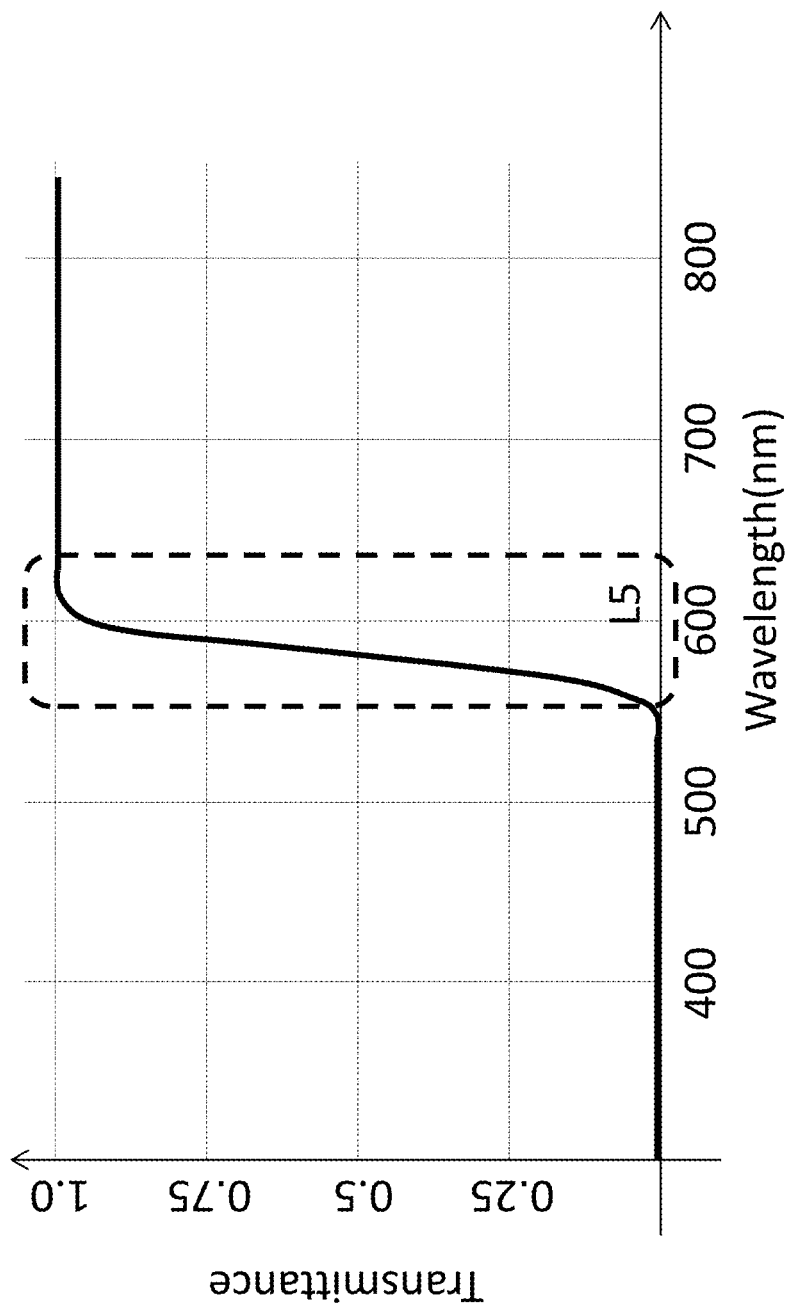
FIG. 7 illustrates the wavelength characteristics of a dichroic mirror according to at least the second embodiment in accordance with one or more aspects of the present disclosure.

With reference to FIGS. 6 and 7, at least a second embodiment of the present disclosure is described herein. At least the second embodiment differs from at least the first embodiment in terms of the use of higher-order diffracted light in the diffractive element 107. Specifically, sixth-order diffracted light, fifth-order diffracted light, and fourth-order diffracted light are used in at least the second embodiment in place of the fifth-order diffracted light, the fourth-order diffracted light, and the third-order diffracted light (as described above for at least the first embodiment). In addition, elements having the same reference characters as used for elements in the following descriptions have functions that are the same or equivalent to those of the first embodiment described above.

Table 3 summarizes parameters of the diffractive element 107 according to at least the second embodiment, and FIG. 6 illustrates the diffraction efficiency of the diffractive element 107 of the subject embodiment. In the second embodiment, sixth-order diffracted light at 415 nm to 475 nm is used as blue illumination light, fifth-order diffracted light at 498 nm to 570 nm is used as green illumination light, and fourth-order diffracted light at 622 nm to 712 nm is used as red illumination light.

TABLE 3

Parameters of the diffractive element 107 according to at least the second embodiment of the present disclosure

|  | Diffractive Element 107 |
| --- | --- |
| pitch (μm) | 1.54 |
| duty cycle | 0.75 |
| depth (μm) | 1.88 |
| refractive index | 1.50 |

When the above settings are employed, a band (L4) in which the diffraction efficiency is low having a wavelength bandwidth of approximately 50 nm is present between 570 nm and 622 nm, as illustrated in FIG. 6. This band is set as a band for color separation of a dichroic mirror. For example, by making the separation wavelength band (L5) coincide with L4 with the use of the dichroic mirror having the wavelength characteristics as illustrated in FIG. 7, a color image may be obtained efficiently without reducing the resolution.

In at least the first embodiment and at least the second embodiment, the separation band of the dichroic mirror may be allocated between the wavelength band for red and the wavelength band for green, but the embodiments of the present disclosure are not limited thereto. For example, the region between green and blue, (e.g., the region L2 in FIG. 3) may be allocated, or a dichroic mirror may be disposed in a low diffraction efficiency region between blue and green and also in a low diffraction efficiency region between green and red (e.g., the regions L1 and L2 in FIG. 3) to dispose three imaging optical systems. However, the bandwidth of the low diffraction efficiency region between blue and green is smaller than the bandwidth of the low diffraction efficiency region between red and green. Thus, the separation band of the dichroic mirror is reduced, and the wavelength characteristics thereof become sharp, which makes it more difficult to design a multilayer film. In addition, when the wavelength bands are separated so as to have three imaging optical systems, the cost for the optical systems greatly increases. On a basis of the above, it is desirable that the separation band of the dichroic mirror be allocated to the low diffraction efficiency region between green and red given such conditions in one or more embodiments.

Figure 8:
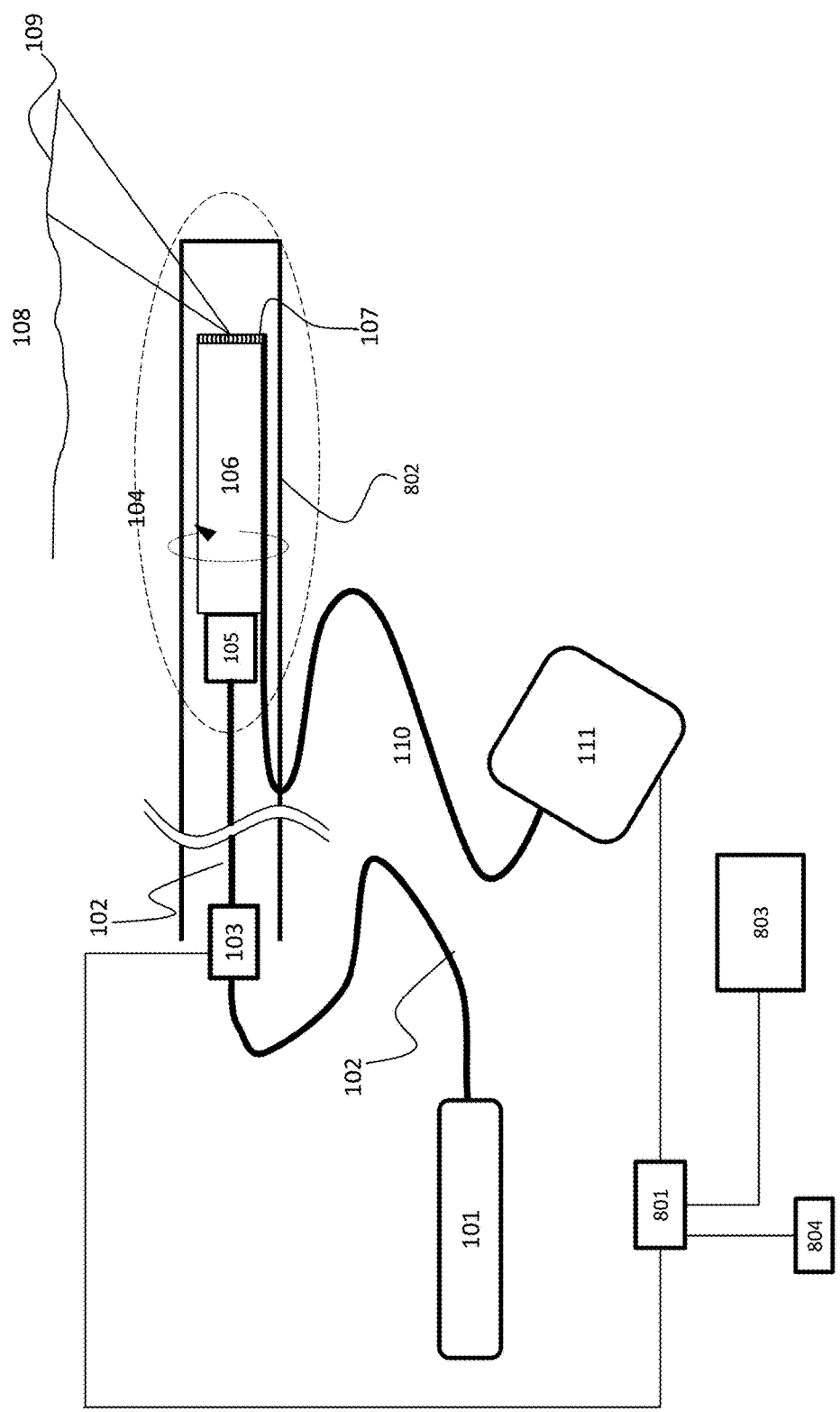
FIG. 8 illustrates an endoscope system according to at least a third embodiment in accordance with one or more aspects of the present disclosure.

With reference to FIG. 8, at least a third embodiment of the present disclosure is described herein. The third embodiment provides an endoscope that includes the optical system used (or similar to the optical system used) in at least the first embodiment. Additionally or alternatively, the spectrometer 111 may be connected to the probe portion 104 via the cable or fiber 110, which in at least one embodiment extends through the probe portion 104 and to the spectrometer 111 prior to passing through the RJ 103 (as best seen in FIG. 8). In FIGS. 1A-1B, with regard to the intensity information of reflected and scattered light acquired by the one-dimensional image sensors 206-1 and 206-2, the information acquired by the one-dimensional image sensor 206-1 is allocated to the blue channel (hereinafter, B channel) and the green channel (hereinafter, G channel) of the image, and the intensity information acquired by the one-dimensional image sensor 206-2 is allocated to the red channel (hereinafter, R channel) of the image. Additionally or alternatively as shown in FIG. 8, these pieces of information may be processed as a single pixel array of RGB in an image processing circuit 801 (which, in one or more embodiments, may be a computer 1200 or 1200' as shown in FIGS. 1A-1B and/or FIGS. 10-11). Here, the probe portion 104 is rotated about the axis extending in the longitudinal direction, and the information in the one-dimensional image sensors 206-1 and 206-2 is read out successively in accordance with the rotation. This pixel array that has been read out is arranged as a single image per rotation of the probe portion 104, and thus a single color image is formed.

Figure 10:
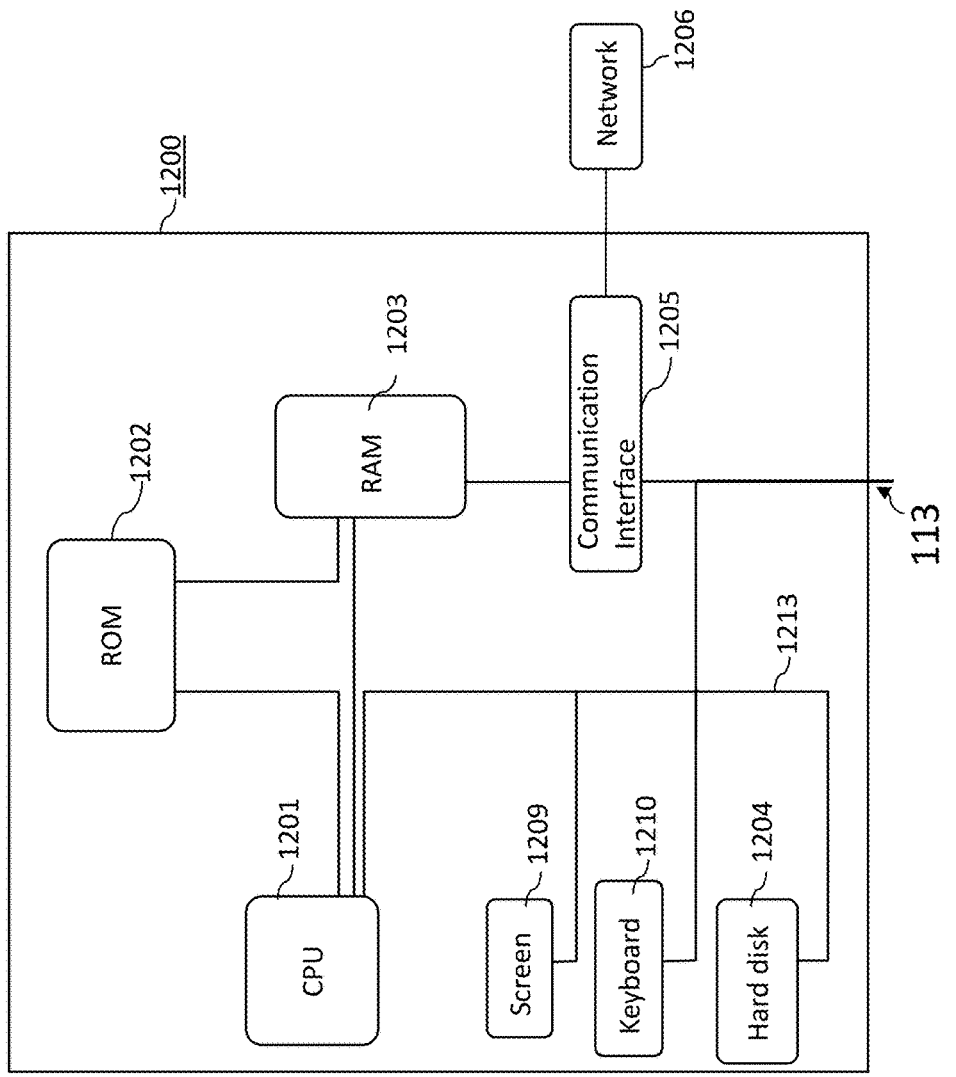
FIG. 10 shows a schematic diagram of an embodiment of a computer that may be used with one or more embodiments of a SEE apparatus or system or an imaging system or one or more methods discussed herein in accordance with one or more aspects of the present disclosure.
Figure 11:
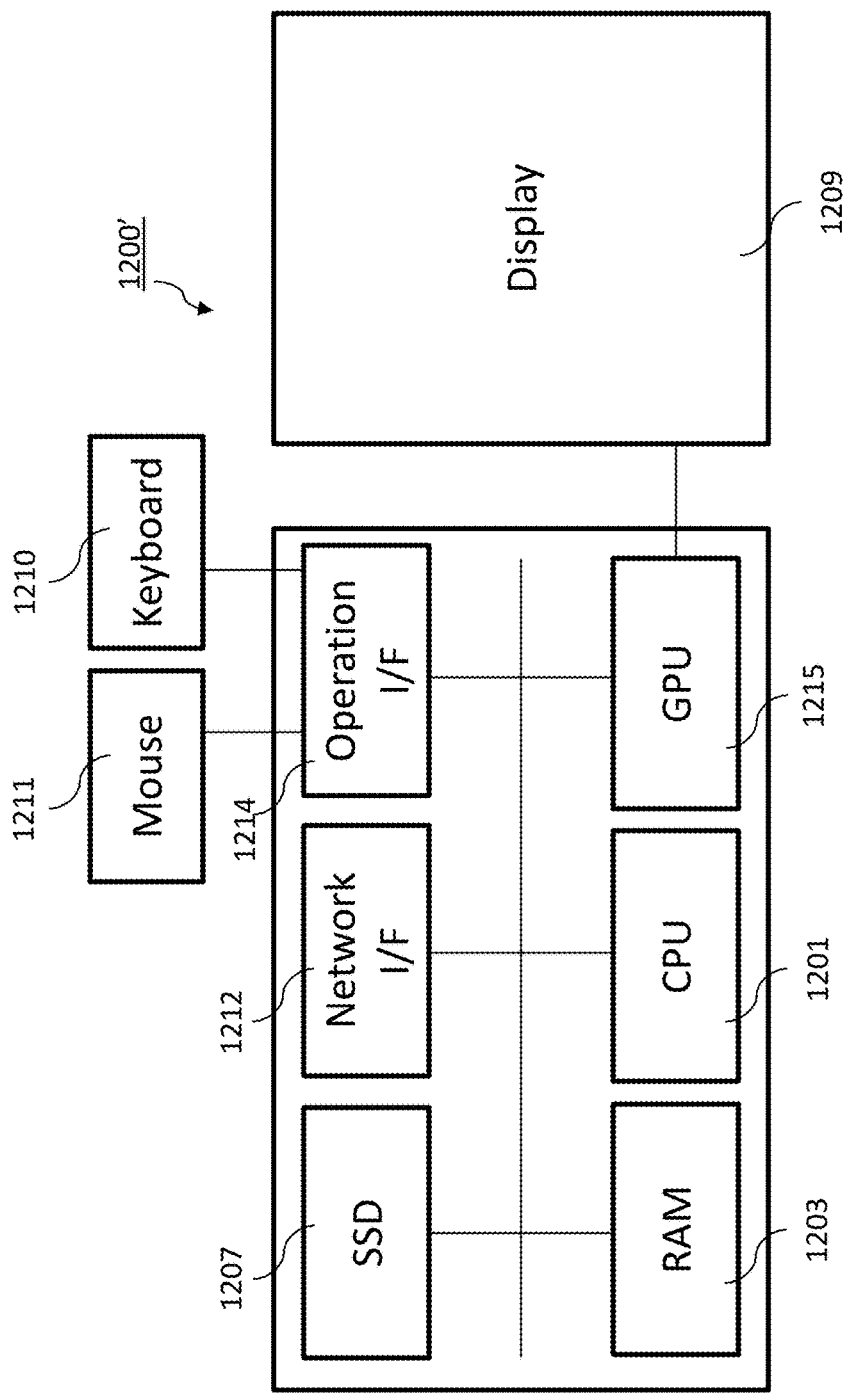
FIG. 11 shows a schematic diagram of another embodiment of a computer that may be used with one or more embodiments of a SEE apparatus or system or an imaging system or methods discussed herein in accordance with one or more aspects of the present disclosure.

The formed image is displayed on a display device 803 (which, in one or more embodiments, may be a display or screen 1209 as shown in FIGS. 10-11 and discussed below) and is stored into a memory 804 (which, in one or more embodiments, may be a hard disk 1204 as shown in FIG. 10 or one or more of the other memories discussed herein).

Here, since the light is separated by using diffraction and since the image sensors 206-1 and 206-2 have the same specifications, the number of pixels on the image sensors for each of the RGB channels is constantly the greatest for R and the smallest for B. However, as described in at least the first embodiment, the final resolution of the image is dependent on the resolution of G due to the characteristics of human eyes. Thus, at the stage of carrying out the image processing, the processing of compressing the number of pixels of R in accordance with the number of pixels of G and the processing of interpolating the number of pixels of B through interpolation or the like are carried out. With this configuration, in one or more embodiments, the image displayed on the display device 803 (which, in one or more embodiments, may be a display or screen 1209 as shown in FIGS. 10-11 and discussed below) at the end becomes an image in which the numbers of pixels of R, G, and B are equal to one another.

This probe portion 104 is inserted into a sheath 802 that is transparent in a measurement wavelength band, and the probe portion 104 rotates inside the sheath 802 (the sheath does not rotate). With this configuration, the probe portion can be inserted into a body cavity and can be used as an endoscope. Any of the probe portions 104 of the one or more embodiments discussed herein may be used with the sheath 802 depending on the use thereof.

Here, the probe portion 104 and the sheath 802 after the RJ 103 may be removed and replaced. After the probe portion 104 and the sheath 802 are inserted into a body, the probe portion 104 and the sheath 802 may be removed and discarded, and a new probe portion may be mounted. Thus, the cleansing process may be reduced, and the cost related to maintenance and building such apparatuses or systems may be reduced.

The endoscope is constituted by an optical fiber for illumination (e.g., the fiber 102 (best shown in FIGS. 1A-1B and 8)) and a detection fiber (e.g., the fiber 110 (best shown in FIGS. 1A-1B and 8), and thus a very thin endoscope having a diameter of approximately 1 mm may be constructed. Accordingly, aside from a digestive organ to which an endoscope is often applied, the endoscope can be applied to a variety of sites, including a circulatory organ, a respiratory organ, and a urinary organ.

Figure 9:
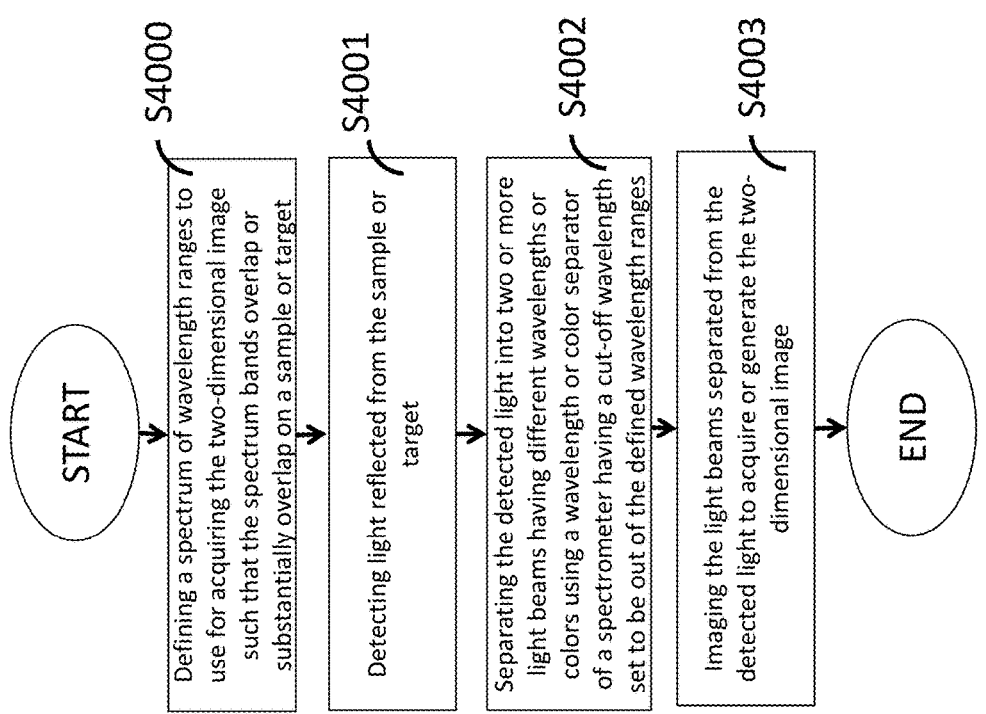
FIG. 9 is a flow diagram showing a method of performing an imaging technique in accordance with one or more aspects of the present disclosure.

In accordance with one or more aspects of the present disclosure, one or more methods for performing two-dimensional imaging are provided herein. FIG. 9 illustrates a flow chart of at least one embodiment of a method for performing two-dimensional imaging. Preferably, the method(s) may include one or more of the following: (i) defining a spectrum of wavelength ranges to use for acquiring the two-dimensional image such that the spectrum bands overlap or substantially overlap on a sample or target (see step S4000 in FIG. 9); (ii) detecting light reflected from the sample or target (see step S4001 in FIG. 9); (iii) separating the detected light into two or more light beams having different wavelengths or colors using a wavelength or color separator of a spectrometer having a cut-off wavelength set to be out of the defined wavelength ranges (see step S4002 in FIG. 9); and imaging the light beams separated from the detected light to acquire or generate the two-dimensional image (see step S4003 in FIG. 9). One or more methods may further include at least one of: using a probe grating to generate the spectrum bands that overlap or substantially overlap on the sample or target; and optimizing the probe grating so that a diffraction efficiency is high within the wavelength ranges. In one or more embodiments, a SEE probe may be connected to one or more systems (e.g., the system 100, the system 100', the system 1000, etc.) with a connection member or interface module. For example, when the connection member or interface module is a rotary junction for a SEE probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the SEE probe may be separate from the detection portion of the SEE probe. For example, in one or more applications, a probe may refer to the illumination assembly, which includes the illumination fiber 102 (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: the detection fiber 110, the spectrometer 111, the computer 1200, the computer 1200', the processing circuit 801, etc. The detection fibers, such as the detection fiber(s) 110, may surround the illumination fiber, such as the IF 102, and the detection fibers may or may not be covered by the grating, such as the grating 107.

Unless otherwise discussed herein, like numerals indicate like elements. For example, while variations or differences exist between the systems, such as, but not limited to, the system 100, the system 100', the system 1100, etc., one or more features thereof may be the same or similar to each other, such as, but not limited to, the light source 101 or other component(s) thereof (e.g., the console 1200, the console 1200', the RJ 103, the probe portion 104, etc.). Those skilled in the art will appreciate that the light source 101, the RJ 103, the MCU 140, the spectrometer 111, the spectrometer 111 (one or more components thereof) and/or one or more other elements of the system 100, may operate in the same or similar fashion to those like-numbered elements of one or more other systems, such as, but not limited to, the system 100', the system 1000, etc. as discussed herein. Those skilled in the art will appreciate that alternative embodiments of the system 100, the system 100', the system 1000, and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100, the system 100', and the system 1000 as discussed herein, there are similarities. Likewise, while the console or computer 1200 may be used in one or more systems (e.g., the system 100, the system 100', the system 1000, etc.), one or more other consoles or computers, such as the console or computer 1200' or the processing circuit 801 (and/or components 803 and 804), may be used additionally or alternatively.

There are many ways to compute intensity, viscosity, resolution (including increasing resolution of one or more images), creation of color images or any other measurement discussed herein, digital as well as analog. In at least one embodiment, a computer, such as the console or computer 1200, 1200', may be dedicated to control and monitor the SEE devices, systems, methods and/or storage mediums described herein.

Various components of a computer system 1200 (see e.g., the console or computer 1200 as shown in FIGS. 1A-1B) are provided in FIG. 10. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 10). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a SEE device or system, such as, but not limited to, the system 100, the system 100', and/or the system moo, discussed herein above, via one or more lines 1213), and one or more other computer systems 1200 may include one or more combinations of the other aforementioned components (e.g., the one or more lines 1213 of the computer 1200 may connect to other components via line 113 (as diagrammatically shown in FIGS. 1A-1B)). The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for SEE tissue characterization, diagnosis, evaluation and imaging. The system 1200 may further include one or more processors connected via a network connection (e.g., via network 1206). The CPU 1201 and any additional processor being used by the system 1200 may be located in the same telecom network or in different telecom networks (e.g., performing SEE technique(s) may be controlled remotely).

The I/O or communication interface 1205 provides communication interfaces to input and output devices, which may include the light source 101, a spectrometer (e.g., the spectrometer 111 (e.g., the communication interface of the computer 1200 may connect to other components via line 113 (as diagrammatically shown in FIGS. 1A-1B and 10))), a microphone, a communication cable and a network (either wired or wireless), a keyboard 1210, a mouse (see e.g., the mouse 1211 as shown in FIG. 11), a touch screen or screen 1209, a light pen and so on. The Monitor interface or screen 1209 provides communication interfaces thereto.

Any methods and/or data of the present disclosure, such as the methods for performing SEE tissue characterization, diagnosis, examination and/or imaging (including, but not limited to, increasing image resolution) with as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 11), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 10. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 10) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 11. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with the MCU 140 and the spectrometer 111 via the operation interface 1214 or the network interface 1212 (e.g., via a cable or fiber, such as the cable or fiber 113 as similarly shown in FIGS. 1A-1B). A computer, such as the computer 1200', may include the MCU 140 in one or more embodiments. The operation interface 1214 is connected with an operation unit such as a mouse device 1211, a keyboard 1210 or a touch panel device. The computer 1200' may include two or more of each component.

At least one computer program is stored in the SSD 1207, and the CPU 1201 loads the at least one program onto the RAM 1203, and executes the instructions in the at least one program to perform one or more processes described herein, as well as the basic input, output, calculation, memory writing and memory reading processes.

The computer, such as the computer 1200, 1200', communicates with the MCU 140 to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a SEE system (e.g., the system 100, the system 100', the system 1000, etc.). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 1000, etc.) to set or change the imaging condition (e.g., improving resolution of an image or images), and to start or end the imaging. The laser source 101 and the spectrometer 111 may have interfaces to communicate with the computers 1200, 1200' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 7,872,759; 7,889,348; 8,045,177; 8,145,018; 8,289,522; 8,838,213; 8,928,889; 9,254,089; 9,295,391; and 9,557,154 to Tearney et al. U.S. Pat. No. 9,332,942 to Jaffer, as well as the disclosures in Patent Application Publication Nos. US 2016/0341951, US 2017/0035281, US 2017/0168232, US 2017/0176736, US 2017/167861, WO2017/024145, WO2017/117203, and WO2017/139657, and U.S. Non-Provisional patent application Ser. No. 15/418,329 filed Jan. 27, 2017 each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. A two-dimensional image acquiring apparatus comprising:
   a Spectrally Encoded Endoscopy ("SEE") probe including at least one diffractive grating or element and one or more optical fibers, the at least one diffractive grating or element operating to separate and diffract a transmitted light into a plurality of separated light beams of different orders such that the diffracted light beams are overlapped or superposed or substantially overlapped or substantially superposed on a target region;
   at least first and second image sensors or detectors that operate to acquire one or more intensities from a detected light;
   at least first and second diffraction gratings or elements, the first diffraction grating or element operating to receive at least a first light beam or a first wavelength band of the detected light, and the second diffraction grating or element operating to receive at least a second light beam or at least a second wavelength band of the detected light; and
   at least first and second imaging optical systems that operate to image a plurality of light beams separated from the detected light, the at least first imaging optical system being disposed between the at least first image sensor or detector and the at least first diffraction grating or element, and the at least second imaging optical system being disposed between the at least second image sensor or detector and the at least second diffraction grating or element,
   wherein the at least one diffractive grating or element of the SEE probe, the at least first and second imaging optical systems, and the at least first and second image sensors or detectors are disposed for each of the plurality of light beams separated from the detected light to acquire spectral data of each of the plurality of light beams separated from the detected light, and
   wherein the at least one diffractive grating or element of the SEE probe operates to rotate such that an image of the at least first and second image sensors or detectors is changed, and a two-dimensional image is acquired from the image.

2. The image acquiring apparatus of claim 1, further comprising a light source that operates to transmit the transmitted light to the SEE probe via at least one of the one or more optical fibers such that:
   (i) the at least one diffractive grating or element is irradiated with the transmitted light;
   (ii) a sample or a target located in the target region is irradiated with the superposed or substantially superposed diffracted light beams; and
   (iii) reflected scattered light from the sample or the target is detected by the at least first and second image sensors or detectors.

3. The image acquiring apparatus of claim 2, wherein the light source is a supercontinuum (SC) light source having a wavelength band from blue to infrared.

4. The image acquiring apparatus of claim 1, wherein the at least first and second imaging optical systems are connected or adjacent to the at least first and second image sensors or detectors, respectively, such that the one or more intensities from the detected light are converted by the at least first and second image sensors or detectors into first and second electric signals.

5. The image acquiring apparatus of claim 4, further comprising one or more of: (i) at least one processor that operates to receive the first and second electric signals and to generate the two-dimensional image; and (ii) a display or a screen that operates to display the generated, two-dimensional image.

6. The image acquiring apparatus of claim 4, further comprising a spectrometer that includes the at least first and second image sensors or detectors, the at least first and second imaging optical systems, at least one color or wavelength separator that operates to separate the detected, transmitted light in accordance with one or more wavelengths into the plurality of separated light beams, and the at least first and second diffraction gratings or elements such that one or more of: (i) the at least one color or wavelength separator is located in between or adjacent to the at least first and second diffraction gratings or elements; (ii) the at least one color or wavelength separator is located optically before both of the at least first and second diffraction gratings or elements; and (iii) the first image sensor or detector and the first imaging optical system is located on one side of the at least one color or wavelength separator and the second image sensor or detector and the second imaging optical system is located on an opposite side of the at least one color or wavelength separator.

7. The image acquiring apparatus of claim 1, further comprising one or more of:
   (i) a spacer element disposed at a distal end of the SEE probe such that the spacer element and the at least one diffractive grating or element are adjacent and/or connected;
   (ii) a gradient-index lens disposed in the SEE probe adjacent or connected to the spacer element;
   (iii) a motor and/or a rotary junction that operates to rotate to the SEE probe;
   (iv) a motion control component that operates to change a speed of the motor and/or the rotary junction; and
   (v) a sheath housing the SEE probe.

8. The image acquiring apparatus of claim 1, further comprising at least one color or wavelength separator that operates to separate the transmitted light in accordance with one or more wavelengths into the plurality of separated light beams,
   wherein one or more of:
   (i) when the two-dimensional image is generated, the at least one color or wavelength separator carries out color separation in a wavelength band in which an efficiency of the at least one diffractive grating or element is lower than that in a wavelength band used to generate the two-dimensional image on a basis of a diffraction efficiency of the at least one diffractive grating or element,
   (ii) the at least second light beam or at least second wavelength band of the detected light comprises a plurality of light beams or a plurality of wavelengths;
   (iii) the wavelength band separated by the at least one color or wavelength separator is between a wavelength band corresponding to a red signal and a wavelength band corresponding to a green signal in a color image, and
   (iv) the at least one color or wavelength separator is a dichroic mirror.

9. The image acquiring apparatus of claim 1, wherein an image sensor is disposed in the vicinity of a focal point of the image sensor.

10. The image acquiring apparatus of claim 1, wherein one or more of:
    (i) the at least first and second image sensors or detectors include two image sensors, the two image sensors being an image sensor configured to acquire spectral data corresponding to a first signal in a color image and an image sensor configured to acquire spectral data corresponding to at least second and third signals, respectively;
    (ii) the first signal is a red signal in a color image and the at least second and third signals are blue and green signals;
    (iii) the at least first and second diffraction gratings or elements include two diffraction elements, the two diffraction elements being a diffraction element configured to separate a wavelength band corresponding to a first signal or a red signal in a color image and a diffractive element configured to separate a wavelength band corresponding to second and third signals or blue and green signals, respectively; and
    (iv) the at least first and second imaging optical systems include two imaging optical systems, the two imaging optical systems being an imaging optical system configured to image a wavelength band corresponding to a first signal or a red signal in a color image and an imaging optical system configured to image a wavelength band corresponding to second and third signals or blue and green signals, respectively.

11. The image acquiring apparatus of claim 10, wherein the wavelength band corresponding to the first signal or the red signal is no less than about 600 nm nor more than about 900 nm, and the wavelength band corresponding to the second and third signals or the blue and green signals is no less than about 400 nm nor more than about 600 nm.

12. The image acquiring apparatus of claim 1, wherein the image acquiring apparatus is an endoscope apparatus.

13. The image acquiring apparatus of claim 1, wherein the one or more optical fibers include: (i) one or more illumination fibers that operate to send light from a light source to the at least one diffractive grating or element to illuminate the target region with light; and (ii) one or more detection fibers that operate to receive light reflected from a target or a sample disposed in the target region and that passes back through the at least one diffractive grating or element and into the one or more detection fibers.

14. A two-dimensional image acquiring apparatus comprising:
    a Spectrally Encoded Endoscopy ("SEE") probe including a first grating and one or more optical fibers, the first grating operating to separate and diffract a light transmitted via a first optical fiber of the one or more optical fibers into a plurality of separated light beams of different orders such that the diffracted light beams are overlapped or superposed or substantially overlapped or substantially superposed on a target region, the one or more optical fibers including a second optical fiber that operates to transmit detected light from the target region on which the diffracted light is incident;
    a wavelength or color separator to separate the light transmitted by the second optical fiber, in accordance with a wavelength into at least two beams of light including a first light beam and a second light beam;
    a second grating operating to diffract the first light beam of the at least two beams;
    a third grating operating to diffract the second light beam of the at least two beams;
    first imaging optics that operate to receive the first light beam diffracted by the second grating, and to provide one or more images;
    second imaging optics that operate to receive the second light beam diffracted by the third grating, and to provide one or more images;
    a first image pickup device arranged such that the first imaging optics are disposed between the first image pickup device and the second grating; and
    a second image pickup device arranged such that the second imaging optics are disposed between the second image pickup device and the third grating,
    wherein a two-dimensional image is obtained from images acquired, while the first grating is rotated, by the first and second image pickup devices,
    wherein the wavelength or color separator separates the transmitted light between a first band of wavelength corresponding to a red signal and a second band of wavelength corresponding to blue and green signals or to a green signal, and
    wherein the first band of wavelength corresponding to the red signal is incident on the second grating and the second band of wavelength corresponding to the blue and green signals or to the green signal is incident on the third grating.

15. A two-dimensional image acquiring apparatus, comprising:

a light source;

a diffractive element, light from the light source being transmitted via a fiber, the diffractive element being irradiated with the transmitted light, a target or subject being irradiated with a light beam separated by the diffractive element in accordance with a wavelength, reflected scattered light from the target or subject being transmitted via a fiber, the diffractive element separating the reflected scattered, transmitted light in accordance with a wavelength;

at least first and second image sensors or detectors that operate to acquire one or more intensities from a detected light of the reflected scattered light;

at least first and second diffraction gratings or elements, the first diffraction grating or element operating to receive at least a first light beam or a first wavelength band of the detected light, and the second diffraction grating or element operating to receive at least a second light beam or at least a second wavelength band of the detected light;

at least first and second imaging optical systems that operate to image a plurality of light beams separated from the detected light, the at least first imaging optical system being disposed between the at least first image sensor or detector and the at least first diffraction grating or element, and the at least second imaging optical system being disposed between the at least second image sensor or detector and the at least second diffraction grating or element, wherein the diffractive element is rotated so as to change an image of the at least first and second image sensors or detectors, and a two-dimensional image is acquired from the image, wherein a wavelength or color separator configured to separate the reflected scattered, transmitted light in accordance with a wavelength is provided, wherein the diffractive element, the at least first and second imaging optical systems, and the at least first and second image sensors or detectors are disposed for each of the light beams separated from the reflected scattered, transmitted light to acquire spectral data of each of the light beams separated from the reflected scattered, transmitted light, wherein the wavelength band separated by the wavelength or color separator is between a wavelength band corresponding to a red signal and a wavelength band corresponding to a blue-green signal or a green signal in a color image, and wherein the band of wavelength corresponding to the red signal is incident on the at least first diffraction grating or element and the band of wavelength corresponding to the blue and green signals or to the green signal is incident on the at least second diffraction grating or element.

16. A method for controlling a two-dimensional image acquiring apparatus, the method comprising:

defining a spectrum of wavelength ranges to use for acquiring the two-dimensional image such that the spectrum bands overlap or substantially overlap on a sample or target;

detecting light reflected from the sample or target;

separating the detected light into two or more light beams having different wavelengths or colors using a wavelength or color separator of a spectrometer having a cut-off wavelength set to be out of the defined wavelength ranges; and imaging the light beams separated from the detected light to acquire or generate the two-dimensional image, wherein one light beam of the two or more light beams is incident on a first grating, is passed from the first grating to a first imaging system operating to image a plurality of light beams separated from the detected light, and is passed from the first imaging system to a first sensor or detector to acquire one or more intensities from the detected light, and wherein a second light beam of the two or more light beams is incident on a second grating, is passed from the second grating to a second imaging system operating to image a plurality of light beams separated from the detected light, and is passed from the second imaging system to a second sensor or detector to acquire one or more intensities from the detected light.

17. The method of claim 16, further comprising using a probe grating to generate the spectrum bands that overlap or substantially overlap on the sample or target.

18. The method of claim 17, further comprising optimizing the probe grating so that a diffraction efficiency is high within the wavelength ranges.

19. The image acquiring apparatus of claim 1, wherein the different orders of the plurality of separated light beams include:
(i) fourth-order light, fifth-order light and sixth-order light; or
(ii) third-order light, fourth-order light and fifth-order light.

20. The image acquiring apparatus of claim 14, wherein the different orders of the plurality of separated light beams include:
(i) fourth-order light, fifth-order light and sixth-order light; or
(ii) third-order light, fourth-order light and fifth-order light.

* * * * *